(12) United States Patent
Greenspan et al.

(10) Patent No.: US 6,291,530 B1
(45) Date of Patent: Sep. 18, 2001

(54) ARYL-SUBSTITUTED ACRYLAMIDES WITH LEUKOTRIENE B4 (LTB-4) RECEPTOR ANTAGONIST ACTIVITY

(75) Inventors: Paul David Greenspan, New Providence; Roger Aki Fujimoto, Morristown, both of NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/269,251

(22) Filed: Mar. 23, 1999

Related U.S. Application Data

(60) Provisional application No. 60/027,468, filed on Sep. 26, 1996.

(51) Int. Cl.[7] .................. A61K 31/165; A61K 31/445; A61K 31/40; A61K 31/535; A61K 31/41
(52) U.S. Cl. ................. 514/617; 514/317; 514/428; 514/237.5; 514/381; 549/76; 548/496; 548/253; 546/194; 546/276.4; 546/268.4; 546/192; 546/124; 544/124; 544/168
(58) Field of Search ................ 564/207; 514/621, 514/617, 317, 237.5, 381; 549/76; 562/450; 546/194, 276.4, 124, 268.4, 192; 548/496, 253; 544/168

(56) References Cited

U.S. PATENT DOCUMENTS

| | | | |
|---|---|---|---|
| 5,210,208 | 5/1993 | Huang et al. | 548/253 |
| 5,232,948 | 8/1993 | Huang et al. | 514/563 |
| 5,344,845 | 9/1994 | Koda et al. | 514/614 |
| 5,488,160 | 1/1996 | Morrissey | 564/165 |
| 5,538,940 | 7/1996 | Sauter et al. | 504/314 |
| 5,569,677 | 10/1996 | Daines . | |
| 5,624,943 | 4/1997 | Heindl et al. | 514/345 |
| 5,631,262 | 5/1997 | Chambers et al. | 514/277 |
| 5,633,258 | 5/1997 | Chambers et al. | 514/277 |
| 5,795,914 | 8/1998 | Konno et al. | 514/562 |

FOREIGN PATENT DOCUMENTS

| | | |
|---|---|---|
| 518 819 | 12/1992 | (EP) . |
| 588 655 | 3/1994 | (EP) . |
| 652 208 A1 | 5/1995 | (EP) . |
| 656 349 | 6/1995 | (EP) . |
| 703 216 | 3/1996 | (EP) . |
| WO 91 18601 | 12/1991 | (WO) . |
| WO 91/18883 | 12/1991 | (WO) . |
| WO91/18601 | 12/1991 | (WO) . |
| WO 93 06085 | 4/1993 | (WO) . |
| WO 93 16036 | 8/1993 | (WO) . |
| WO 94/00437 * | 1/1994 | (WO) . |
| WO 94 02464 | 2/1994 | (WO) . |
| WO 94/06761 | 3/1994 | (WO) . |
| WO 94 11341 | 5/1994 | (WO) . |
| WO 97/11069 | 3/1997 | (WO) . |
| WO 98/13347 | 4/1998 | (WO) . |

OTHER PUBLICATIONS

Konno, M. et al., Adv. Prostagl. Thromb. Leukotr. Res., vol. 21, pp. 411–414 (1990).
Djuric, S.W. et al., Drugs Future, vol. 17, No. 9, pp. 819–830 (1992).
Greenspan, P.D. et al., Bioorganic & Medicinal Chemistry Letters, vol. 7, No. 7, pp. 949–954 (1997).
Huang et al., J. Med. Chem. vol. 39, pp. 3748–3755 (1996).
Chan W.K. et al., J. Med. Chem., vol. 39, pp. 3756–3768 (1996).
Mutoh R. et al. Heterocycles, vol. 41, No. 1, pp. 9–12 (1995).

* cited by examiner

*Primary Examiner*—Alan L. Rotman
*Assistant Examiner*—Binta Robinson
(74) *Attorney, Agent, or Firm*—Norbert Gruenfeld

(57) ABSTRACT

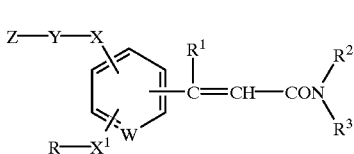

(I)

Disclosed are compounds of formula (I) wherein W is CH or N; R is (mono- or di cabocyclic or heterocyclic aryl)-lower alkyl; $R^1$ is hydrogen or lower alkyl; $R^2$ and $R^3$ are hydrogen, lower alkyl, lower alkoxy-lower alkyl or aryl-lower alkyl; or $R^2$ and $R^3$ joined together represent lower alkylene optionally interrupted by O, NH, N-lower alkyl or S so as to form a ring with the amide nitrogen; X is O, S, SO, $S_2$ or a direct bond; $X^1$ is O, S, SO, $SO_2$ or a direct bond; Y is a direct bond, lower alkylene or lower alkylidene; and Z is carboxyl, 5-tetrazolyl,, hydroxymethyl or carboxyl derivatized in the form of a pharmaceutically acceptable ester, and pharmaceutically acceptable salts thereof; which arm useful as LTB-4 antagonists.

12 Claims, No Drawings

ARYL-SUBSTITUTED ACRYLAMIDES WITH LEUKOTRIENE B4 (LTB-4) RECEPTOR ANTAGONIST ACTIVITY

CROSS REFERENCE TO RELATED APPLICATIONS

This application claims the benefit of Provisional Application No. 60/027,468 filed Sep. 26, 1996.

SUMMARY OF THE INVENTION

The invention relates to the aryl-substituted acrylamides as defined herein which are particularly useful as selective Leukotriene B-4 (LTB-4) receptor antagonists, methods for preparation thereof, pharmaceutical compositions comprising said compounds, and a method of antagonizing LTB-4 and of treating conditions or syndromes in mammals which are responsive to LTB-4 antagonism using said compounds or pharmaceutical compositions comprising said compounds of the invention.

Leukotriene B-4 (LTB-4) is an important inflammatory mediator being a potent chemotactic agent and activator of polymorphonuclear leucocytes (PMN's) and monocytes. It modulates the production and effects of other important inflammatory mediators, e.g. interleukin-1 and gamma interferon. LTB-4 has been implicated in the pathogenesis of a number of inflammatory diseases, such as rheumatoid arthritis, inflammatory bowel disease, psorasis on-steroidal-antiinflammatory drug-induced gastropathy, adult respiratory distress syndrome (ARDS), myocardial infarction, allergic rhinitis, hemodialysis-induced neutropenia, late phase asthma, ocular conditions such as ocular allergy and inflammation, dermatitis such as atopic and contact dermatitis, and chronic obstructive pulmonary disorders, such as chronic bronchitis.

The compounds of the invention which are useful as selective LTB-4 antagonists can be used for the treatment of the above-cited LTB-4 dependent conditions.

DETAILED DESCRIPTION OF THE INVENTION

The invention relates to substituted acrylamides of formula I

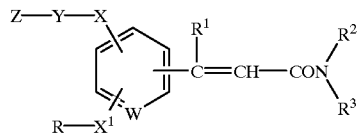

(I)

wherein W is CH or N;

R is (mono- or di-carbocyclic aryl or mono- or di-heterocyclic aryl)-lower alkyl;

$R^1$ is hydrogen or lower alkyl;

$R^2$ and $R^3$ are hydrogen, lower akyl, lower alkoxy-lower alkyl or aryl-lower alkyl; or $R^2$ and $R^3$ joined together represent lower alkylene optionally interrupted by O, NH, N-lower alkyl or S so as to form a ring with the amide nitrogen;

X is O, S, SO, $SO_2$ or a direct bend;

$X^1$ is O, S, SO, $SO_2$ or a direct bond;

Y is a direct bond, lower alkylene or lower alkylidene; and

Z is carboxyl, 5-tetrazolyl, hydroxymethyl or carboxyl derivatized in form of a pharmaceutically acceptable ester;

and pharmaceutically acceptable salts thereof.

Preferred are compounds of formnula Ia

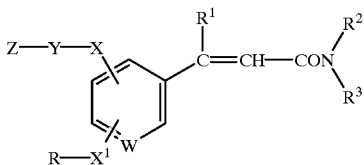

(Ia)

wherein R, $R_1$, $R_2$, $R_3$, X, $X^1$, Y and Z have meaning as defined above, and pharmaceutically acceptable salts thereof.

Preferred in turn are said compounds wherein, when W is CH, each of the substituents —X—Y—Z and —$X^1$—R is located at either the meta (3) or para (4) positions or at either of the two meta (3 and 3') positions of the phenyl ring; and wherein, when W is N, each of the said substituents is at either of the adjacent 5 and 6 positions of the pyridine ring; and pharmaceutically acceptable sats thereof.

The particular embodiments of the invention relate to the compounds of formula II

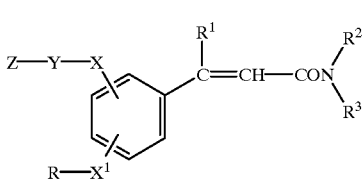

(II)

and of formula III

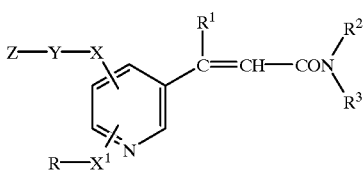

(III)

wherein in formula II the substituents —X—Y—Z and —$X^1$—R are located at the meta (3) and para (4) positions or at the two meta (3 and 3') positions and wherein in formula III the said substituents are at adjacent 5 and 6 positions of the pyridine ring;

R is (mono or di-carbocyclic aryl or mono- or di-heterocyclic aryl)-lower alkyl;

$R^1$ is hydrogen or lower alkyl;

$R^2$ and $R^3$ are hydrogen, lower alkyl, lower alkoxy-lower alkyl or aryl-lower alkyl; or $R^2$ and $R^3$ together with the nitrogen to which they are attached represent pyrrolidino, piperidino, or morpholino;

X is O, S or a direct bond;

$X^1$ is O, S or a direct bond;

Y is a direct bond, lower alkylene or lower alkylidene; and

Z is carboxyl, 5-tetrazolyl, hydroxymethyl or carboxyl derivatized in form of a pharmaceutically acceptable ester; and pharmaceutically acceptable salts thereof.

A particular embodiment of the invention relates to compounds of formula I, II or III wherein each of X and $X^1$ is oxygen, and R, $R^1$, $R^2$, $R^3$, Y and Z have meaning as defined above.

Another particular embodiment of the invention relates to compounds of formula

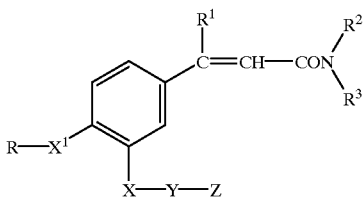

(IV)

or of formula IVa

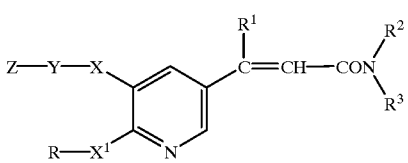

(IVa)

wherein R is (mono- or di-carbocyclic aryl or mono- or di-heterocyclic aryl)-lower alkyl;

$R^1$ is hydrogen or lower alkyl, $R^2$ and $R^3$ are hydrogen, lower alkyl, lowe alkoxy-lower alkyl or aryl-lower alkyl; or $R^2$ and $R^3$ together with the nitrogen which they are attached represent pyrrolidino, piperidino or morpholino;

X is O, S or a direct bond;

$X^1$ is O, S or a direct bond;

Y is $C_1$–$C_4$-alkylene or $C_1$–$C_4$-alkylidene;

Z is carboxyl, 5-tetrazolyl, hydroxymethyl or carboxyl derivatized in form of a pharmaceutically acceptable ester; and pharmaceutically acceptable salts thereof.

In view of the presence of a double bond as part of the structure, the substituted acrylamides of the invention exist in either two geometric isomeric forms, namely as cis or trans isomers (also denoted as Z and E isomers).

Preferred are the E-isomers (or trans isomers), illustrated by the cinnamides of

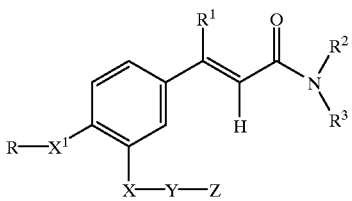

(IVb)

in which the substituted phenyl and the

groups are trans to each other.

Preferred compounds include the E-isomers of compounds of formulae I, II, III, IV and IVa in which R is (mono- or di-carbocyclic aryl)-lower alkyl; $R^1$ is lower alkyl; $R^2$ and $R^3$ represent lower alkyl; X represents oxygen (O) or a direct bond; $X^1$ represents oxygen (O); Y represents lower alkylene or lower alkylidene; Z represents carboxyl or 5-tetrazolyl; and pharmaceutically acceptable salts thereof.

Similarly preferred are E-pyridylacrylamides (E-isomers corresponding to compounds of formula IVa) in which X, Y, Z, $X^1$, R, $R^1$, $R^2$ and $R^3$ have meaning as defined for compounds of formula IVb above.

The definitions as such or in combination as used herein, unless denoted otherwise, have the following meanings within the scope of the present invention.

Aryl represents carbocyclic or heterocyclic aryl, either monocyclic or bicyclic.

Monocyclic carbocyclic aryl reprsents optionally substituted phenyl, being preferably phenyl or phenyl substituted by one to three substituents, such being advantageously lower alkyl, hydroxy, lower alkoxy, acyloxy, halogen, cyano or trifluoromethyl.

Bicyclic carbocyclic aryl represents 1- or 2-naphthyl or 1- or 2-naphthyl preferably substituted by lower alkyl, lower alkoxy or halogen.

Monocyclic heterocyclic aryl represents preferably optionally substituted thiazolyl, thienyl, furanyl or pyridyl.

Optionally substituted furanyl represents 2- or 3-furanyl or 2- or 3-furanyl preferably substituted by lower alkyl.

Optionally substituted pyridyl represents 2-, 3- or 4-pyridyl 2-, 3- or 4-pyridyl preferably substituted by lower alkyl, halogen or cyano.

Optionally substituted thienyl represents 2- or 3-thienyl 2- or 3-thienyl preferably substituted by lower alkyl.

Optionally substituted thiazolyl represents e.g. 4-thiazolyl, or 4-thiazolyl substituted by lower alkyl.

Bicyclic heterocyclic aryl represents preferably indolyl or benzothiazolyl optionally substituted by hydroxy, lower alkyl, lower alkoxy or halogen, advantageously 3-indolyl or 2-benzothiazolyl.

Aryl as in aryl-lower alkyl is preferably phenyl or phenyl substituted by one or two of lower alkyl, lower alkoxy, hydroxy, lower alkanoyloxy, halogen, trifluoromethyl or cyano; also, optionally substituted naphthyl.

Aryl-lower alkyl is advantageotsly benzyl or 1- or 2-phenethyl optionally substituted on phenyl by one or two of lower alkyl, lower alkoxy, hydroxy, lower alkanoyloxy, halogen, cyano or trifluoromethyl.

The term "lower" referred to herein in connection with organic radicals or compounds respectively defines such with up to and including 7, preferably up and including 4 and advantageously one or two carbon atoms. Such may be straight chain or branched.

A lower alkyl group preferably contains 1–4 carbon atoms and represents for example ethyl, propyl, butyl or advantaeously methyl.

A lower alkoxy group preferably contains 1–4 carbon atoms and represents for example methoxy, propoxy, isopropoxy or advantageously ethoxy.

A lower alkoxycarbonyl group preferably contains 1 to 4 carbon atoms in the alkoxy portion and represents, for example, methoxycarbonyl, propoxycarbonyl, isopropoxycarbonyl or advantageously ethoxycarbonyl.

Lower alkylene preferably contains 1–4 carbon atoms and represents for example methylene, ethylene, 1,2 or 1,3-propylene and the like.

Lower alkylidene is lower alkylene, preferably $C_1$–$C_4$-alkylene in which the two attached groups are attached to the same carbon of the lower alkylene chain, and represents for example ethylidene or propylidene, e.g. 1,1 or 2,2-propylidene.

Halogen (halo) preferably represents fluoro or chloro, but may also be bromo or iodo.

Acyl is derived from a carboxylic acid and represents preferably optionally substituted lower alkanoyl, carbocyclic aryl-lower alkanoyl, aroyl, lower alkoxycarbonyl or aryl-lower alkoxycarbonyl, advantageously optionally substituted lower alkanoyl, or aroyl.

Lower alkanoyl is preferably acetyl, propionyl, butyryl, or pivaloyl.

Optionally substituted lower alkanoyl for example represents lower alkanoyl or lower alkanoyl substituted by lower alkoxycarbonyl, lower alkanoyloxy, lower alkanoylthio, lower alkoxy, or by lower alkylthio.

Aroyl is preferably monocyclic carbocyclic or monocyclic heterocyclic aroyl.

Monocyclic carbocyclic aroyl is preferably benzoyl or benzoyl substituted by lower alkyl, lower alkoxy, halogen or trifluoromethyl.

Monocyclic heterocyclic aroyl is preferably pyridylcarbonyl or thienylcarbonyl.

Acyloxy is preferably optionally substituted lower alkanoyloxy, lower alkoxycarbonyloxy, monocyclic carbocylic aroyloxy or monocyclic heterocyclic aroyloxy.

Aryl-lower alkoxycarbonyl is preferably monocyclic carbocyclic-lower alkoxycarbonyl, advantageously benzyloxycarbonyl.

Pharmaceutically acceptable esters are preferably prodrug ester derivatives, such being convertible by solvolysis or under physiological conditions to the free carboxylic acids of formula I.

Pharmaceutically acceptable prodrug esters are preferably e.g. lower alkyl esters, aryl-lower alkyl esters, α-(lower alkanoyloxy)-lower alkyl esters such as the pivaloyloxymethyl ester, and α-(lower alkoxycarbonyl- or di-lower alkylamino carbonyl-)-lower alkyl esters.

Pharmaceutically acceptable salts are salts derived from pharmaceutically acceptable bases for any acidic compounds of the invention, e.g. those wherein Z represents carboxyl. Such are e.g. alkali metal salts (e.g. sodium, potassium salts), alkaline earth metal salts (e.g. magnesium, calcium salts), amine salts (e.g. tromethamine salts).

The compounds of the invention exhibit valuable pharmacological properties in mammals, and are particularly useful as selective Leukotriene B-4 (LTB-4) receptor antagonists, e.g. for the treatment of a condition or syndrome in a mammal responsive to the selective antagonism of LTB-4 receptors, such as rheumatoid arthritis, inflammatory bowel disease, psoriasis, non-steroidal-antiinflammatory-drug-induced gastropathy, adult respiratory distress syndrome (ARDS), myocardial infarction, allergic rhinitis, hemodialysis-induced neutropenia, and late phase asthma. The compounds of the invention are also useful for the treatment of ocular conditions, such as ocular allergy and inflammation, and also for the treatment of dermatitis, e.g. atopic and contact dermatitis; and also for the treatment of chronic obstructive pulmonary disorders such as chronic bronchitis.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously orally or intravenously, e.g. as a suspension or in aqueous solution. The dosage in vitro may range between about $10^{-6}$ molar and $10^{-9}$ molar concentrations. The dosage in vivo may range depending on the route of administration, between about 0.1 and 50 mg/kg, advantageously about 1 and 25 mg/kg.

In vitro testing is most appropriate for the free carboxylic acids of the invention. The test compound is dissolved in dimethyl sulfoxide, ethanol, or 0.25 M sodium bicarbonate solution, and the solution is diluted with buffer to the desired concentration.

Biological effects are evaluated in pharmacological tests generally known in the art, e.g. as illustrated below.

LTB-4 receptor binding is dete mined in the following assay involving receptor binding of $[H^3]$-LTB-4 to intact human neutrophils.

LTB-4 is purchased as a solution in either ethanol or DMSO (Biomol, Plymouth Meeting, Pa.) and diluted into Hank's balanced Salt Solution (HBSS) before use. For in vitro tests, test compounds are dissolved in DMSO to produce stock solution of 10 mM. Dilutions are made so that the final concentration of DMSO is 0.35%.

Neutrophils are prepared from nitrated human venous blood. Blood (25 ml) is mixed with HESPAN (15 ml) (DuPont, Wilmington, Del.) and allowed to stand at room temperature for 40 minutes. The supernatant is removed and centrifuged for 10 minutes at 400×g. The resulting pellet is resuspended in phosphate-buffered saline without calcium and magnesium (GIBCO, Grand Islands N.Y.). Thirty-five ml of the resuspended cells is layered over 15 ml of Ficoll-Paque (Sigma, St Louis, Mo.) and then centrifuged for 15 minutes at 420×g. The resulting cell pllet is resuspended in 10 ml of phosphate-buffered saline without calcium and magnesium. Twenty-five ml of deionized water are added to the suspension for 20 seconds followed by the same volume of buffer at twice the normal concentration. The suspension is centrifuged for 5 minutes at 200×g, and the pellet resuspended in Hank's Balanced Salt Solution (HBSS).

Binding of $[H^3]$-LTB-4 to neutrophils is measured as described by Gorman and Lin, Methods Enzymol. 141: 372–378 (1987) and Jackson et al., J. Pharmacol.Exp. Ther., Vol. 262, p. 80 (1992). Intact human ntutrophils (3×106) are added to HBSS containing 0.5 nM $[H^3]$-LTB-4 (specific activity 32 Ci/mmol, DuPont-NEN, Boston, Mass.) and compound (final volume 0.5 ml). After incubating for 20 minutes at 0° C., the bound radioactivity is collected on Whatman GF/C filters by vacuum filtration using a Brandel harvester. The filters are washed twice with ice cold HBSS. Filters are counted using Formula-989 scintillation cocktail (DuPont-NEN, Boston, Mass.). Non-specific binding is determined in the presence of 300 nM LTB-4 (Biomol Res. Labs, Plymouth Meeting, Pa.).

Inhibition of LTB-4 is determined by measuring the inhibition of the LTB-4-induced intracellular calcium rise in human neutrophils. Increases in intracellular Ca++ are measured as described by Seligmann et al., Agents and Actions, Vol. 21, p. 375 (1987). Neutrophils are purified from citrated human venous blood by sedimentation in HESPAN as described above. Neutrophils are isolated from the resulting pellet by centrifugal elutriation (Berkow et al., J. Lab. Clin. Med., Vol. 104, p. 698, 1984). Except were noted the neutrophils are incubated with acetoxymetbyl ester of Fura-2 (0.2 μM)(Molecular Probes Inc.) for 30 minutes at 37° C. in HEPES-buffered Hank's solution containing Ca++ and Mg++. The Fura-2 loaded cells are washed and stored on ice at a concentration of 2×106 cells/ml in 10 mM HEPES-buffered HBSS without Ca++ and Mg++. Fifteen minutes before assay, 1.5 ml of the cell suspension is mixed with 10 μl of 0.15 M Ca++ and 0.15 M Mg++ by stirring at 37° C. Compounds are added 40 seconds before the addition of 1 nM LTB-4. The change in fluorescence was followed using a DMX 1000 spectrofluorometer (SLM-Aminco Instruments, Urbana Ill.).

Antiinflammatory activity can be demonstrated in vivo in the mouse ear model by measuring the inhibition of arachidonic acid-induced mouse ear inflammation. The methodology used is essentially that described by Young et al., J. Invest. Dermatol. 82, 367–371 (1984). Female mice (A/J, Jakson Labs., Bar Harbor, Me.) weighing 20 gm are divided into groups consisting of six mice per treatment group. They are fasted overnight. Arachidonic acid (2 mg in 15 μl acetone) (Sigma, St Louis, Mo.) is applied to the inner surface of the right ear. The left ear received 15 μl of acetone. The animals are sacrificed one hour later. Compounds are orally administered 30 minutes before the application of arachidonic acid using 3% fortified cornstarch, 5% polyethylene glycol 400 and 0.34% tween 80 as the vehicle. Edema is determined by subtracting the weight of the left ear punch from that of the right ear. As the marker for neutrophil infiltration, myeloperoxidase activity is measured as described by Bradley et al., J. Invest. Dermatol., Vol. 78, p. 206 (1982). The right ear punches from the both the vehicle and compound treated groups are used. The percentage of inhibition is calculated by comparing the myeloperoxidase activity of the compound treated groups with those of the vehicle treated group.

The trinitrobenzenesulfonic acid-induced chronic colitis test in the rat, e.g. as described by Wallace et al, Gastroenterlogy 1989, 96, 29–36, can be used to evaluate compounds for effects indicative of utility in inflammatory bowel diseases.

Illustrative of the invention, the compounds of examples 2y, 8a and 8b have $IC_{50}$'s of about 48, 87 and 74 nM, respectively, in the LTB-4 receptor binding assay. Said compounds inhibit edema and myeloperoxidase activity in the arachidonic acid-induced mouse ear inflammation model at a dose of 3 mg/Kg p.o. at 1.5 hours post administration and at a dose of 10 mg/Kg p.o. at 18 hours post administration. Calcium rise is inhibited at a concentration of about 18, 22 and 8 nM, respectively.

The compounds of the invention (as illustrated for compounds of formula II) can be prepared as follows:

(a) by condensing e.g. a compound of the formula

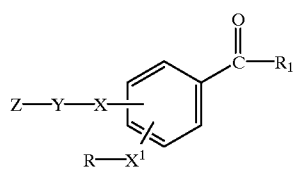

(V)

werein R, $R^1$, X, $X^1$, Y and Z have meaning as defined above and any reactive groups within R, $R^1$, X, $X^1$, Y and Z are in protected form, with a diester of phosphonic acid of the formula

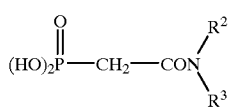

(VI)

under conditions of a Horner-Emmons condensation, e.g. in the presence of an anhydrous base; or (b) by condensing a compound 4 the formula

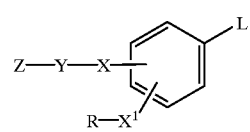

(VII)

wherein X, Y, Z, R and $X^1$ have meaning as defined hereinabove and L is a leaving group with a compound of the formula

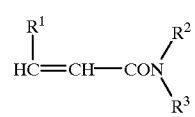

(VIII)

wherein $R^1$, $R^2$ and $R^3$ have meaning defined above under conditions of a Heck olefination, e.g. in the presence of a palladium salt, triarylphosphine and a base; or (c) converting a carboxylic acid of the formula

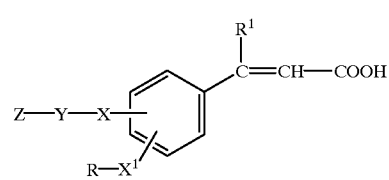

(IX)

or a functional reactive derivative thereof into an amide of formula I; and (d) converting a compound of the formula

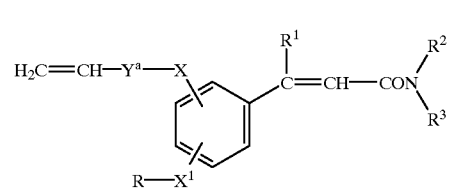

(X)

wherein R, $R^1$, $R^2$, $R^3$, $X^1$ have meaning as defined above, X represents a direct bond and $y^a$ represents $CH_2$, to a compound of formula II wherein X represents a direct bond and Y represents $CH_2CH_2$; and (e) converting a compound of the formula XI

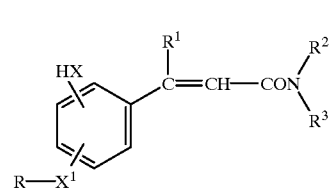

(XI)

wherein R, $R^1$, $R^2$, $R^3$ and $X^1$ have meaing as defined above and X represents O or S to a compound of formula II wherein X represents O or S and Y is lower alkylene or lower alkylidene; by treatment with a compound of the formula $$L—Y—Z \qquad (XII)$$

wherein L is a leaving group; Y is lower alkylene and Z has meaning as defined above or advantageously a protected form thereof; or by treatment first with acetone and then chloroform in base to give a compound of formula II wherein Y is isopropylidene and Z is carboxyl.

(f) in above process, if temporarily protecting any interfering reactive group(s), removing said protecting group(s), and then isolating the resulting compound of the invention; and, if desired, converting any resulting compound of the invention into another compound of the invention; and/or, if desired, converting a free carboxylic acid function into a pharmaceutically acceptable ester derivative, converting a resulting ester into the free acid or into another ester derivative; and/or, if desired, converting a resulting free compound into a salt or a resulting salt into the free compound or into another salt, and/or, if desired, separating a mixture of geometric isomers and/or racemates obtained into the single isomers or racemates, and/or, if desired, resolving a racemate obtained into the optical antipodes.

The pyridyl compounds of formula III can be similarly prepared.

In starting compounds and intermediates which are converted to the compounds of the invention in manner described herein, functional group present, such as thiol, carboxyl, amino and hydroxy groups, are optionally protected by conventional protecting groups that are common in preparative organic chemistry. Protected thiol, carboxyl, amino and hydroxy groups are those that can be converted under mild conditions into free thiol, carboxyl, amino and hydroxy groups without other undesired side reactions taking place.

The purpose of introducing proecting groups is to protect the functional groups from undesired reactions with reaction components and under the conditions used from carrying out a desired chemical transformation. The need and choice of protecting groups for a particular reaction is known to those skilled in the art and depends on the nature of the functional group to be protected (thiol, carboxyl, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, N.Y. 1973, T. W. Greene and P. G. M. Woots, "Protective Groups in Organic Synthesis", Wiley, N.Y. 1991, and also in "The Peptides", Vol. I, Schroeder and Luebke, Academic Press, London, N.Y., 1965.

The compounds of the invention are prepared by sequences of reactions, the individual reactions being carried out for the most part by methodology generally known in the art or as illustrated herein.

The condensation according to process (a) of e.g. a ketone of formula V with a diester of a phosphonic acid of the forula VI is carried out under the conditions of a Horner-Emmons condensation, in the presence of a suitable anhydrous base such as sodium hydride in an inert solvent such as tetrahydrofuran, preferably at reflux temperature.

Esters of the phosphonic acids of formula VI are preferably lower alkyl diesters, such as the ethyl or methyl diesters.

Prior to condensation, any reactive functional groups such as hydroxy, carboxyl and the like may first be protected e.g. in the form of esters and ethers well known in the art.

The olefin obtained by the Honer-Emmons condensation is primarily the E-isomer (in which the aryl nucleus and the

substituent are trans). The corresponding Z-isomer (in which the aryl nucleus and the

substituent are cis) is also formed as a minor product. The ratio of geometric isomers is dependent on the substitution and reaction conditions involved.

The starting materials of formula V are known or are prepared according to methodology known in the art and illustated herein.

For example, starting materials of formula V wherein X and $X^1$ are oxygen are prepared from the corresponding dihydroxyacetophenone (wherein $R^1$ is methyl) which is first alkylated with a reactive derivative of the alcohol corresponding to R, (e.g. a benzyl halide) in the presence of a base (e.g. with lithium carbonate in DMF), followed by alkylation with e.g. Z-substituted alkyl halide wherein Z is in protected form (such as ethyl bromoacetate) in the presence of a base (e.g. with potassium carbonate in acetone). The reverse order of the alkylations can also be used.

For the preparation of compounds wherein Z is hydroxy, alkylation with e.g. an alkyl halide substituted by protected hydroxy (preferably hydroxy protected in form of a tetrahydropyranyl ether) can be used. The hydroxy protecting group is removed after the Horner-Emmons condensation.

For preparation of starting materials of formula V wherein one of X and $X^1$ is sulfur and the other is O, a mono methylated dihydroxyacetophenone is first treated with N,N-dimethylthiocarbamoyl chloride in the presence of base (e.g. potassium hydroxide). The resulting O-(dimethylaminothiocarbonyl) derivative is rearranged thermally (according to methodology docribed in Synthesis 1992, 112) at elevated temperature to obtain the corresponding S-(dimethylaminocarbonyl) derivative, which is in turn treated with base (e.g. KOH/water, ethylene glycol) to obtain the O-methylated-SH- substituted acetophenone. S-alkylation followed by O-dimethylation (e.g. with $BBr_3$ in methylene chloride) and subsequent O-alkylation as described above yields the starting material of formula wherein one of X and $X^1$ is sulfur and the other of X and $X^1$ is oxygen.

The starting materials of formula V wherein one of X and $X^1$ is a direct bond and the other of X and $X^1$ is oxygen can be prepared e.g. from dihydroxyacetophenone as follows.

For example, a compound of formula V wherein $R^1$ is methyl, Z—Y—X— represents ethoxycarbonylmethoxy and R—$X^1$— represents phenylpropyl can be prepared by treating mono-hydroxy-mono-ethoxycarbonylmethoxy substituted acetophenone with trifluoromethanesulfonic acid anhydride to obtain the corresponding trifluoromethanesulfonoxy derivative.

Coupling with phenylacetylene according to Tetrahedron Letters 27, 1171 (1986) in the presence of e.g. $[(C_6H_5)_3P]_2$, $PdCl_2$ and CuI followed by catalytic hydrogenation of the obtained phenylacetylenyl substituted compound yields said derivative of formula V wherein R-$X^1$ represents phenylpropyl.

The pyridyl starting materials corrsponding to compounds of formula V which are suitable for the preparation of compounds of formula III in which X and $X^1$ are oxygen can be prepared e.g. as illustrated herein.

For example, 5-bromo3-hydroxy-2 (1H)-pyridinone is protected as the 3-t-butyloxycarbonyl derivative (by treatment with di-t-butyl dicarbonate) and treated with e.g. an appropriately substituted benzyl bromide in the presence of silver carbonate in an inert solvent such as toluene. The resulting 2-benzyloxy substituted derivative is then reacted with cuprous cyanide in an inert solvent such as DMF at elevated temperature to yield 6-benzyloxy-5-hydroxynicotinonitrile. Condensation with a Grignard reagent (e.g. methylmagnesium bromide) yields 6-benzyloxy-5-hydroxy-3-acetylpyridine which is further reacted, with e.g. ethyl bromoacetate, to give the starting material for the Horner-Emmons condensation of process (a).

The condensation according to process (b) is carried out under the conditions generally known for a Heck olefination reaction (see e.g. Organic Reactions, 27, 345 (1982)), as illustrated herein.

The leaving group L in a compound of formula VII is preferably halo (advantageously bromo) or trifluoromethanesulfonyloxy.

The Heck olefination of a compound of formula VII with an olefin of formula VIII (e.g. N,N-diethylcrotonamide) is carried out in the presence of a base (e.g. triethylamine) a palladium salt (e.g. Pd $(OAc)_2$) and a triarylphosphine (e.g. tri-o-tolylphosphine) at elevated temperature (e.g. at 75°–125° C.).

Starting materials of VII are prepared according to methods known in the art and illustrated herein.

The substituted acrylamides of formula VIII are generally known in the art.

The conversion according to process (c) of a carboxylic acid of formula IX or a functional reactive derivative thereof into an amide of formula II is carried out by methodology well known in the art for conversion of a carboxylic acid to an amide.

Useful reactive derivatives of the carboxylic acids of formula IX are, for example, activated esters, reactive mixed anhydrides, and acid halides (such as the acid chloride, prepared e.g. with oxalyl chloride). A caboxylic acid of formula IX can also be condensed with the appropriate amine in the presence of a suitable condensing agent, for example, 1-(3-dimethylaminopropyl)-3-ethylcarbodiimide or dicyclohexylcarbodiimide, and a basic tertiary amine, e.g. dimethylaminopyridine, in an inert solvent such as methylene chloride. Carboxylic acid starting materials of formula IX can be prepared by Heck condensation of compounds of formula VII, with e.g. crotonic acid in the presence of e.g. Pd $(OAc)_2$, tri (o-tolyl)phosphine and triethylamine.

Process (d) can be carried out by subjecting a starting material of formula X to rhodium catalyzed hydroboration and oxidation to obtain the corresponding terminal alcohol (compound of formula II wherein Z is hydroxymethyl).

The hydroboration reaction is carried out according to Manning et al., Angew. Chem. Int. Ed. 24, 878 (1985), e.g. with Wilkinson's catalyst (tris-(triphenylphosphine) rhodium (I) chloride) and catecholborane in an inert solvent such as tetrahydrofuran, followed by hydrogen peroxide in base (e.g. sodium hydroxide).

The resulting alcohol can then be oxidized to a corresponding carboxylic acid (Z=carboxyl) of formula 1 using e.g. a two step procedure, first by reaction with oxalyl chloride and DMSO, followed by treatment with sodium chlorite in the presence of disodium phosphate and isobutylene.

The starting materials of formula X, e.g. wherein the substituents are on adjacent carbons and wherein $X^1$ is O can be prepared as follows.

For example, p-hydroxyacetophenone is converted to the allyl ether (with allyl bromide, $K_2CO_3$ in acetone) which is in turn subjected to a Claisen rearrangement to give m-allyl-p-hydroxyacetophenone which is in turn 0-alkylated and subjected to a Horner-Emmons reaction according to process (a) so as to give the corresponding intermediate of formula X.

Process (e), involving the condensation of a compound of formula XI and XII can be carried under normal alkylation procedures known in the art, e.g. with a Z-substituted alkyl halide wherein Z is preferably in protected form (such as ethyl bromoacetate or 3-(tetrahydropyranyloxy)-propylbromide) in the presence of a base (e.g. potassium carbonate in acetone).

Condensation of a compound of formula XI first with acetone and then chloroform is carried out in acetone as the solvent in the presence of a strong base (such as solid sodium hydroxide) as illustrated herein, The starting materials of formula XI can be prepared as described under process (a) and the starting materials of formula XII are generally known in the art.

Certain compounds of the invention and intermediates can be converted to each other according to general reactions well-known in the art.

For instance, compounds wherein Z is hydroxy may be converted to compounds wherein Z is carboxyl by oxidation e.g. first to the aldehyde with dimethylsulfoxide and oxalyl chloride, followed by treatment with e.g. pyridinium dichromate to obtain the carboxylic acid. Carboxylic acid esters may be hydrolyzed to acids under basic conditions, e.g. with dilute sodium hydroxide in methanol.

Carboxylic acid esters may in turn be prepared from the corresponding carboxylic acids by condensation with e.g. the halide corresponding to the esterifying alcohol in the presence of a base, or with an excess of the alcohol in the presence of acid catalyst.

Depending on the choice of starting materials and methods, the new compounds nd intermediates may be in the form of one of the possible isomers or mixtures thereof, for example, as substantially pure geometric (cis or trans) isomers, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound.

Alternately, optically active isomers may be prepared from optically active starting materials.

Finally, the compounds of the invention are either obtained in the free form, or as a salt thereof.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical composition according to the invention are those suitable for enteral, such as oral or rectal, transdermal and parenteral administration to mammals, including man, to antagonize $LTB_4$ receptors, and for the treatment of a condition or syndrome responsive to the selective anagonism of $LTB_4$ receptors, comprising an effective amount of a pharmacologically active compound of the invention, alone or in combination, with one or more pharmaceutically acceptable carriers.

The novel pharmaceutical products contain, for example, from about 10% to about 80%, preferably from about 20% to about 60%, of the active compound. Examples of pharmaceutical products according to the invention for enteral or parenteral administration are those in dose-unit forms such as coated tablets, tablets, capsules or suppositories, as well as ampoules. These are prepared in a manner known per se, for example using conventional mixing, granulating, coating, dissolving or freeze-drying processes. Thus, pharmaceutical products for oral use can be obtained by combining the active compound with solid excipients, where appropriate granulating a mixture which is obtained, and processing the mixture or granules, if desired or necessary, after addition of suitable auxiliaries to tablets or cores of coated lablets.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. Cores of coated tablets are provided with suitable, optionally enteric, coatings, using, inter alia, concentrated sugar solutions which optionally contain gum arabic, talc, polyvinylpyrrolidone, polyethylene glycol and/or titanium dioxide, lacquer solutions in suitable organic solvents or solvent mixtures or, for the preparation of enteric coatings, solutions of suitable cellulose products such as acetyl cellulose phthalate or hydroxypropylmethylcellulose phthalate. Colorants or pigments can be added to the tablets or coatings of coated tablets, for example, to identify or to indicate various doses of active compound. In addition, they may also contain other therapeutically valuable substances. Said compositions are prepared according to conventional mixing, granulating or coating methods, respectively, and contain about 0.1 to 75%, preferable about 1 to 50%, of the active ingredient.

Suitable formulations for topical application, e.g. to the skin and eyes, are preferably aqueous solutions, ointments, creams or gels well-known in the art.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable formulations for the treatment of pulmonary disorders include aerosols which are well-known in the art.

In conjunction with another active ingredient, a compound of the invention may be administered either simultaneously, before or after the other active ingredient, either separately by the same or different route of administration or together in the same pharmaceutical formulation.

The invention further particularly relates to a method for the treatment of a condition or syndrome responsive to the selective antagonism of $LTB_4$ receptors, such as rheumatoid arthritis, inflammatory bowel disease, psoriasis, non-steroidal antiinflammatory-drug-induced gastropathy, adult respiratory distress syndrome (ARDS), myocardial infarction, allergic rhinitis, hemodialysis-induced neutropenia, and late phase asthma; also for the treatment of ocular allergies and inflammations; also for the treatment of atopic and contact dermatitis; and also for the treatment of chronic obstructive pulmonary disease such as chronic bronchitis.

The dosage of active compound administered is dependent on the species of warm-blooded animal (mammal), the body weight, age and individual condition, and on the form of administration. A unit dosage for oral administration to a mammal of about 70 kg may contain e.g. between about 1 and about 1000 mg/kg per day of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials are confirmed by standard analytical methods, e.g. microanalysis and spectroscopic characteristics (e.g. MS, IR, NMR). Abbreviations used are those conventional in the art.

EXAMPLE 1

(a) To a solution of diethyl [2-(diethylamino)-2-oxoethyl]-phosphonate (6.9 g, 27.45 mmol) in tetrahydrofuran (150 mL) is added sodium hydride (1.1 g, 27.45 mmol) in one portion. The solution is then stirred at room temperature until clear. A solution of ethyl [5-acetyl-2-(2,6-difluorobenzyloxy)-phenoxy]-acetate (8.0 g, 21.96 mmol) in tetrahydrofuran (50 mL) is added, and the mixture is refluxed for 18 hours. After cooling, the mixture is then quenched with saturated aqueous ammonium chloride (50 mL), and extracted with ethyl acetate (2×150 mL). The combined organic phase is washed with water (1×100 mL) and brine (1×100 mL), dried over $MgSO_4$, concentrated in vacuo, chromatographed (ether) and the major product is recrystallized from ether to yield ethyl (E)-[5-(2-diethylcarbamoyl-1-methylvinyl)-2-(2,6-difluorobenzyloxy)-phenoxy]-acetate, m.p.=73°–76°.

The starting material is prepared as follows:

A mixture of 3',4'-dihydroxyacetophenone (25.0 g, 164.3 mmol), lithium carbonate (12.1 g, 164.3 mmol), and α-bromo-2,6-difluorotoluene (34.0 g, 164.3 mmol) in dimethyl formamide (400 mL) is stirred at room temperature for 2 days. The mixture is then filtered through celite, and the filtrate is concentrated in vacuo. The residue is diluted with $H_2O$(200 mL), and the mixture is filtered. The collected solid is recrystallized from ethanol to give 3'-hydroxy-4'-(2,6-difluorobenzyloxy)-acetophenone.

A mixture of 3'-hydroxy-4'-(2,6-difluorobenzyloxy)-acetophenone (15.0 g, 53.96 mmol), ethyl bromoacetate (7.2 mL, 64.75 mmo), and $K_2CO_3$ (14.9 g, 107.92 mmol) in acetone (350 mL) is refluxed 18 hours. After cooling, the mixture is filtered, and the filtrate is concentrated in vacuo. Recrystallizaton from EtOAc yields ethyl [5-acetyl-2-(2,6-difluorobenzyloxy)-phenoxy]-acetate.

Prepared similarly are:
(b) Ethyl (E)-[5-(2-diethylcarbamoyl-1-methylvinyl)-2-(1-phenylethoxy)-phenoxy]-acetate; MS: 440 ($M^+$+1), 336(M+-$PhCH_2CH_3$), $^1H$ NMR: s(1H) @ 6.14, q(1H) @ 5.32, q(2H) @ 4.25, t(3H) @ 1.33
(c) Ethyl (E)-{5-(2-diethylcarbamoyl-1-methylvinyl)-2-[1-(4-fluorophenyl)-ethoxy]-phenoxy}-acetate; MS: 458 ($M^+$+1), 336 ($M^+$-(4-Ph)$CH_2CH_3$.
(d) Ethyl (E)-[5-(2-diethylcarbamoyl-1-methylvinyl)-2-(2-bromobenzyloxy)-phenoxy]-acetate; MS: 504, 506 ($M^+$+1)
(e) Ethyl (E)-[5-(2-diethylcarbamoyl-1-methylvinyl)-2-(2,6-dichlorobenzyloxy)-phenoxy]-acetate; MS: 494 ($M^+$+1), 334 ($M^+$-(2,6-dichlorophenyl)$CH_2^+$).
(f) Ethyl (E)-[5-(2-diethylcarbamoyl-1-methylvinyl)-2-(2-chlorobenzyloxy)-phenoxy]-acetate; MS: 460 ($M^+$+1).
(g) Ethyl (E)-[5-(2-diethylcarbamoyl-1-methylvinyl)-2-(2,4,6-trimethylbenzyloxy)-phenoxy]-acetate; 460 ($M^+$+1), 336 ($M^+$-2,4,6-trimethylphenyl$^+$), 133 (2,4,6-trimethylbenzyl$^+$).
(h) Ethyl (E)-[5-(2-diethylcarbamoyl-1-methylvinyl)-2-(thiophen-3-yl-methoxy)-phenoxy]-acetate; MS: 432 ($M^+$+1).
(i) Ethyl (E)-[5-(2-diethylcarbamoyl-1-methylvinyl)-2-(2-fluorobenzyloxy)-phenoxy]-acetate; $^1H$ NMR ($CDCl_3$): d(2H) @ 7.92 t(4H) @ 7.00; dd (1H), 7.60;d (1H @ 6.19.
(j) Ethyl (E)-[5-(2-diethylcarbamoyl-1-methylvinyl)-2-(2-fluoro-6-chlorobenzyloxy)-phenoxy]-acetate; MS: 478 ($M^+$+1).
(k) Ethyl (E)-[5-(2-diethylcarbamoyl-1-methylvinyl)-2-(thiophen-2-ylmethoxy)-phenoxy]-acetate; MS: 432 ($M^+$+1), 334 ($M^+$-(thiophene)$CH_2$.
(l) Ethyl (E)-[5-(2-diethylcarbamoyl-1-methylvinyl)-2-(2-cyanobenzyloxy)-phenoxy]-acetate, m.p.=93–96°.

EXAMPLE 2

(a) To a solution of ethyl [5-(2-diethylcarbamoyl-1-methylvinyl)-2-(2,6-difluoro-benzyloxy)-phenoxy]-acetate (2.1 g, 4.55 mmol) in methanol (30 mL) is added IN NaOH (13.7 mL, 13.7 mmol), and the mixture is stirred at room temperature for 2 hours. The solution is then acidified to pH 1 with 1 N HCl, and the mixture is extracted with EtOAc (2×100 mL). The combined organic phase is washed with water (1×100 mL) and brine (1×100 mL), dried over $MgSO_4$, and concentrated in vacuo. The resulting solid is triturated from ether, giving [5-(2-diethylcarbamoyl-1-inethylvinyl)2-(2,6-difluorobenzyloxy)-phenoxy]-acetic acid; m.p.=120°–122°.

Prepared similarly are:
(b) (E)-[5-(2-Diethylcarbamoyl-1-methylvinyl)-2-(1-phenylethoxy)-phenoxy]-acetic acid; m.p.=85°–87°.
(c) (E)-[5-(2-Diethylcarbamoyl-1-methylvinyl)-2-(diphenylmethoxy)-phenoxy]-acetic acid; m.p.=127°–129°.
(d) (E)-4-[5-(2-Diethylcarbamoyl-1-methylvinyl-2-(1-phenylethoxy)-phenoxy]-butanoic acid; MS: 440 ($M^+$+1), 336 ($M^+$-$PhCH_2CH_3$), $^1H$ NMR ($CDCl_3$): q(1H) @ 5.30, t(2H) @ 4.11, 2.65; quint (2H) @ 2.28).
(e) (E)-{5-(2-Diethylcarbamoyl-1methylvinyl)-2-[1-(4-fluorophenyl)-ethoxy]-phenoxy}-acetic acid; m.p.= 102°–104°.
(f) (E)-[5-(2-Diethylcarbamoyl-1-methylvinyl)-2-(2-bromobenzyloxy)-phenoxy]acetic acid; m.p.=96°–99°.
(g) (E)-[5-(2-Diethyicarbamoyl-1-methylvinyl)-2-(2-chlorobenzyloxy)-phenoxy]acetic acid; m.p.=83°–87°.
(h) (E)-{5-(2-Diethylcarbamoyl-1-methylvinyl)-2-[di-(4-fluorophenyl)-methoxy]-phenoxy)}-acetic acid; m.p.= 140°–142°.
(i) (E)-[5-(2-Diethylcarbamoyl-1-methylvinyl)-2-(2-methylbenzyloxy)-phenoxy]-acetic acid, m.p.=84°–86°.
(j) (E)-[5-(2-Diisopropylcarbamoyl-1-methylvinyl)-2-(1-phenylethoxy)-phenoxy]-acetic acid; m.p.=119°–121°.
(k) (E)-[5-(2-Diethylcarbamyl-1-methylvinyl)-2-(2-methoxybenzyloxy)-phenoxy]-acetic acid m.p.=160°–163°.
(l) (E)-[5-(2-Diethylcarbamoyl-1-methylvinyl)2-(benzyloxy)-phenoxy]-acetic acid; m.p.=87°–90°.
(m) (E)-[5-(2-Diethylcarbamoyl-1-methylvinyl)-2-(2,6-dichlorobenzyloxy)-phenoxy]-acetic acid; m.p.=163°–165°.
(n) (E)-[5-(2-Diethylcarbamoyl-1-methylvinyl)-2-(2-fluorobenzyloxy)-phenoxy]-acetic acid; m.p.=99°–101°.
(o) (E)-[5-(2-Diethylcarbamoyl-1-methylvinyl)-2-(thiophen-2-ylmethoxy)-phenoxy]-acetic acid; MS: 404 ($M^+$+1).
(p) (E)-{5-(2-Diethylcarbamoyl-1-methylvinyl)-2-[2-(trifluoromethyl)-benzyloxy]-phenoxy}-acetic acid; m.p.= 126°–129°.
(q) (E)-[5-(2-Diethylcarbamoyl-1-methylvinyl)-2-(2,4,6-trimethylbenzyloxy)-phenoxy]-acetic acid m.p.=160°–162°.
(r) (E)-[5-(2-Diethylcarbamoyl-1-methylvinyl)-2-(2,4-dichlorobenzyloxy)-phenoxy]-acetic acid; m.p.=145°–147°.
(s) (E)-[5-(2-Diethylcarbamoyl-1-methylvinyl)-2-(2,5-dichlorobenzyloxy)-phenoxy]-acetic acid; m.p.=142°–146°.
(t) (E)-[5-(2-Diethylcarbamoyl-1-methylvinyl)-2-(naphth-1-ylmethoxy)-phenoxy]-acetic acid; MS: 448 ($M^+$+1).
(u) (E)-[5-(2-Diethylcarbamoyl-1-methylvinyl)-2-(naphth-2-yl-methoxy)-phenoxy]-acetic acid; MS: 448 ($M^+$+1), 430 ($M^+$-$H_2O$).
(v) (E)-{5-(2-Diethylcarbamoyl-1-methylvinyl)-2-[ 1-(2-fluorophenyl)-ethoxy]-phenoxy }-acetic acid; m.p.= 94°–98°.
(w) (E)-{5-(2-Diethylcarbamoyl-1-methylvinyl)-2-[1-(2-chlorophenyl)-ethoxy]-phenoxy)}-acetic acid, MS: 446 ($M^+$+1), 308 ($M^+$-(4-Cl-phenyl)$CH_2CH_3$).
(x) (E)-[5-(2-Diethylcarbamoyl-1-methylvinyl)-2-(thiophen-3-yl-methoxy)phenoxy]-acetic acid; m.p.= 127°–128°.

(y) (E)-[5-(2-Diethylcarbamoyl-1-methylvinyl)-2-(2,6-difluorobenzyloxy)-phenoxy]-acetic acid; m.p.=120°–122°.

(z) (E)-[5-(2-Diethylcarbamoyl-1-methylvinyl)-2-(furan-2-yl-methoxy)-phenoxy]-acetic acid; m.p.=123.5°124.5°.

(aa) (E)-[5-(2-Diethylcarbamoyl-1-methylvinyl)-2-(2,3,4,5,6-pentafluorobenzyl-oxy)-phenoxy]-acetic acid; m.p.=100°–103°.

(bb) (E)-[5-(2-Diethylcarbamoyl-1-methylvinyl)-2-(2-chloro-6-fluorobenzyl-oxy)-phenoxy]-acetic acid m.p.=143°–146°.

(cc) (E)-[5-(2-Diethylcarbamoyl-1-methylvinyl)-2-(2-cyanobenzyloxy)-phenoxy]-acetic acid mp.=110°–112°.

(dd) (E)-{5-[2-(Di-(2-methoxyethyl))-carbamoyl-1-methylvinyl]-2-(1-phenylethoxy)-phenoxy}-acetic acid; m.p.=114°.

(ee) (E)-{5-[2-(Di-(2-methoxyethyl))-carbamoyl-1-methylvinyl]-2-(2,6-difluorobenzyloxy)-phenoxy }-acetic acid; m.p.=105°.

(ff) (E)-{5-[2-(Di-(2-ethoxyetyl))-carbamoyl-1-methylvinyl]-2-(2,6-difluorobenzyloxy)-phenoxy}-acetic acid; m.p.=105°.

EXAMPLE 3

(a) A solution of [5-(2-diethycarbamoyl-1-methylvinyl)-2-(1-phenylethoxy)-phenoxy]-acetic acid (300 mg, 0.97 mmol), 4-dimethylaminopyridine (12 mg, 0.097 mmol) and isopropanol (117 mg, 1.95 mmol) in methylene chloride (30 mL) is cooled to 0° C., and 1-(3-dimethylaminopropyl)-3-etbylcarbodiimide.HCl (205 mg, 1.07 mmol) is added in one portion. The mixture is then allowed to stir at room temperature for 18 hours. After washing with water (50 ml), the organic layer is washed with saturated NaHCO$_3$ (50 mL) and brine (50 mL), dried over Na$_2$SO$_4$ and concentrated in vacuo. Chromatography (silica, 1:1 EtOAc/hexane) yields isopropyl (E)-[5-(2-diethylcarbamoyl-1-methylvinyl)-2-(1-phenylethoxy)-phenoxy]-acetate MS: 454 (M$^+$+1), 350 (M$^+$-PhCHCH$_3^+$).

Similarly prepared are:

(b) Methyl (E)-[5-(2-diethylcarbamoyl-1-methylvinyl)-2-(1-phenylethoxy)-phenoxy]-acetate; MS: 426 (M$^+$+1) 322 (M$^+$-PhCHCH$_3^+$).

(c) Morpholinoethyl (E)-[5-(2-diethylcarbamoyl-1-methylvinyl)-2-(1-phenyl-ethoxy)-phenoxy]-acetate; MS: 525 (M$^+$+1), 421 (M$^+$-PhCHCH$_3^+$).

(d) Butyl (E)-[5-(2-diethylcarbamoyl-1-methylvinyl)-2-(1-phenylethoxy)-phenoxy]-acetate; MS: 468 (M$^+$+1), 364 (M$^+$-PhCHCH$_3^+$).

EXAMPLE 4

A solution of (E)-[5-(2-Diethylcarbamoyl-1-methylvinyl)-2-(1-phenylethoxy)-phenoxy]-acetic acid (250 mg, 0.61 mmol), diethyl 2-chloroacetamide (137 mg, 0.91 mmol), and K$_2$CO$_3$ (126 mg, 0.91 mmol) in dimethyl formamide (30 mL) is stirred overnight at 60°. The mixture is then diluted with 60 mL water and 10 mL saturated aqueous LiCl and the resulting solution is extracted with ether (2×50 mL). The combined organic phase is washed with water (1×100 mL) and brine (1×100), dried over MgSO$_4$, and concentrated in vacuo. Chromatography (silica, EtOAc) yields(E))-[5-(2-diethylcarbamoyl-1-methylvinyl)-2-(1-phenylethoxy)-phenoxy]-acetic acid diethylcarbamoyl-methyl ester; MS: 525 (M$^+$+1), 421 M$^+$-PhCHCH$_3^+$).

EXAMPLE 5

A solution of (E)-3-[4-(1-phenylethboxy)-3-hydroxyphenyl]-2-butenoic acid diethyl amide (0.61 g. 1.73 mmol) and crushed NaOH (0.69 g, 17.3 mmol) in acetone (30 mL) is refluxed 10 minutes and cooled. To this solution is added CHCl$_3$ (0.36 mL, 4.50 mmol), dropwise, and then the solution is refluxed 3 hours. After cooling, the solution is concentrated in vacuo, and the residue is dissolved in H$_2$O (50 mL), and washed with ether (3×50 mL). The aqueous phase is acidified to pH 1 with 1 N HCl, and then extracted with EtOAc (2×30 mL). The combined organic phase is washed with water (1×50 mL) and brine (1×50 mL), dried over MgSO$_4$, and concentrated in vacuo. Recrystallization from ether yields (E)-2-[5-(2-diethylcarbamoyl-1-methylvinyl)-2-(1-phenylethoxy)-phenoxy]-2-methylpropionic acid, m.p. 117°–119°.

The starting material is prepared as follows:

To a solution of washed NaH (0.283 g, 7.06 mmol) in tetrahydrofuran (10 mL) is added a solution of diethyl [2-(diethylamino)-2-oxoethyl]-phosphonate (1.77 g, 7.06 mmol) in THF (10 mL, dropwise, and the solution is stirred at room temperature for 5 minutes until gas evolution ceases. A solution of 4-(1-phenylethoxy)-3-hydroxyacetophenone (1.01 g, 3.53 mmol) in THF (20 mL) is then added over 5 minutes and the resulting mixture is refluxed for 18 hours. After cooling, the mixture is quenched with 30 mL saturated aqueous NH$_4$Cl, and is concentrated to 30 mL in vacuo. The residue is dissolved in EtOAc (50 mL), washed with H$_2$O (1×50 mL) and brine (1×50 mL), dried over MgSO$_4$, and concentrated in vacuo. Chromatography (silica, 2:1 hexane/EtOAc) provides (E)-3-[4-(1-phenylethoxy)-3-hydroxyphenyl]-2-butenoic acid diethyl amide.

EXAMPLE 6

(a) Similarly to procedure described in example 1, ethyl (E)-[5-acetyl-3-(1-phenylethoxy)-phenoxy]-acetate is transformed into ethyl (E)-[5-(2-diethylcarbamoyl-1-methylvinyl)-3-(1-phenylethoxy)-phenoxy]-acetate; MS: 440 (M$^+$+1), 336 (M$^+$-PhCH$_2$CH$_3$).

The starting material is prepared as follows:

To a solution of 3',5'-dihydroxyacetophenone (10.0 g, 66 mmol) and ethyl bromoacetate (11.0 g, 66 mmol) in acetone (300 mL) is added K$_2$CO$_3$ (9.0 g, 66 mmol), and the resulting mixture is refluxed for 3 hours. After cooling, the mixture is filtered, and the filtrate is concentrated in vacuo. The residue is chromatographed (silica, 3:2 hexane/EtOAc) to give a mixture of (3-acetyl-5-hydroxyphenoxy)-acetic acid ethyl ester, 3',5'-dihydroxyacetophenone and [3-acetyl-5-(ethoxycarbonylmethoxy)-phenoxy]-acetic acid ethyl ester (the dialkylation product), which is carried on to the next step without further purification. To a solution of ethyl (3-acetyl-5-hydroxyphenoxy)-acetate (2.4 g, 10.1 mmol), contaminated with 3',5'-dihydroxyacetophenone and (3-acetyl-5-methoxycarbonylmethoxyphenoxy) acetic acid ethyl ester, and (1-bromoethyl)benzene (2.24 g, 12.1 mmol) in acetone (100 mL) is added K$_2$CO$_3$ (2.09 g, 15.1 mmol), and the resulting mixture is refluxed for 3 hours. After cooling, the mixture is filtered, and the filtrate is concentrated in vacuo. The residue is chromatographed (silica, 3:1 hexane/EtOAc) to give ethyl [5-acetyl-3-(1-phenylethoxy)-phenoxy]-acetate.

(b) Similarly prepared is ethyl (E)-[5-(2-diethylcarbamoyl-1-methylvinyl)-3-(1-phenylethoxy)-phenoxy]-acetate; MS: 426 (M$^+$+1).

EXAMPLE 7

(a) Similarly to procedure described in example 2, [5-(2-diethylcarbamoyl-1-methylvinyl)-3-(1-phenylethoxy)- phenoxy]-acetic acid ethyl ester is converted into (E)-[5-(2-di-ethylcarbamoyl-1-methylvinyl)-3-(1-phenylethoxy)-phenoxy]-acetic acid; MS: 412 (M⁺+1), 308 (M⁺-PhCHCH₃⁺); ¹H NMR (CDCl₃): t(3H) @ 6.52, 6.44, 6.39 (arom. H).

Similarly prepared are:

(b) (E)-[5-(2-diethylcarbamoyl-1-methylvinyl)-3-benzyloxyphenoxy]-acetic acid; m.p.=114°–115°.

(c) (E)-[5-(2-diethylcarbamoyl-1-methylvinyl)-3-(2-fluorobenzyloxy)-phenoxy]-acetic acid; m.p.=100°–101°.

(d) (E)-[5-(2-diethyicarbamoyl-1-methylvinyl)-3-(2-chlorobenzyloxy)-phenoxy]-acetic acid; MS: 432 (M⁺+1).

(e) (E)-[5-(2-diethylcarbamoyl-1-methylvinyl)-3-(2,6-difluorobenzyloxy)-phenoxy]-acetic acid; m.p.=116°118°.

EXAMPLE 8

(a) To a solution of (E)-[5-(2-diethylcarbamoyl-1-methylvinyl)-2-(2,6-difluorobenzyloxy)-phenyl]-acetaldehyde (4.38 g, 10.92 mmol) and 2 M isobutylene in THF (36.6 mL, 73.2 mmol) in tBuOH (70 mL) is added a solution of NaClO₂ (1.58 g, 17.48 mmol) and NaH₂PO₄.H₂O (1.96 g, 14.2 mmol) in H₂O (25 mL), and the mixture is stirred at room temperature for 1.5 hours. The mixture is then acidified to pH 3 with 1 N HCl, and then extracted with ether (3×150 mL). The combined organic layers are then extracted with 1 N NaOH (3×150 mL), and the combined aqueous layers are acidified to pH 3 with conc. HCl, and then extracted with EtOAc(3×10). The combined organic phase is washed with water (1×50 mL) and brine (1×50 mL), dried over MgSO₄, and concentrated in vacuo. Recrystallization from MeOH/EtOAc yields (E)-[5-(2-diethylcarbamoyl-1-methyl-vinyl)-2-(2,6-difluorobenzyloxy)-phenyl]-acetic acid; m.p.=167°–168°.

The starting material is prepared as follows:

A solution of (5-bromo-2-methoxyphenyl)acetic acid (20.0 g, 81.6 mmol) in THF (400 mL) cooled to 0°, followed by dropwise addition of 1M BH₃.THF in THF (122.4 mL, 122.4 mmol). After addition is complete, the solution is warmed to room temperature and stirring is continued for 1 hour. At this time, the reaction is cooled back to 0° and quenched with water (50 mL). The mixture is concentrated to 80 mL in vacuo, and the residue is extracted with EtOAc (3×150 mL). Te combined organic phase is washed with water (1×50 mL) and brine (1×50 mL), dried over MgSO₄, and concentrated in vacuo to give 2-(5-bromo-2-methoxyphenyl)-1-ethanol.

To a solution of 2-(5-bromo-2-ethoxyphenyl)-1-ethanol (18.86 g, 81.65 mmol) in 400 mL CH₂Cl₂ at −78° is added boron tribromide (16.98 mL, 179.6 mmol) dropwise, via syringe. After stirring at −78° for 15 minutes, the solution is warmed to room temperature and stirred for 1 hour. The reaction niuture is then poured into ice water (500 mL), shaken, and separated. The organic phase is wshed with water (1×250 mL) and brine (1×100 mL), dried over MgSO₄, and concentrated in vacuo. Chromatography (silica, 2:1 hexane/EtOAc) yields 2-(5-bromo-2-hydroxyphenyl)-1-ethanol.

To a solution of 2-(5-bromo-2-hydroxyphenyl)-1-ethano (9.6 g, 44.2 mmol) and α-bromo-2,6-difluorotoluene (9.16 g, 44.2 mmol) in acetone (500 mL) is added K₂CO₃ (12.21 g, 88.5 mmol), and the mixture is refluxed for 4 hours. After cooling, the mixture is filtered, and the filtrate concentrated in vacuo. The residue is then chromatographed (silica, 4:1 hexane/EtOAc) to yield 2-[5-bromo-2-(2,6-difluorobenzyloxy)phenyl]-1-ethanol.

A solution of 2-[5-bromo-2-[2,6-difluorobenzyloxy)phenyl]-1-ethanol (14.07 g, 41.02 mmol) and N,N-diethylcrotonamide (8.68 g, 61.53 mmol) in 60 mL triethylamine in a thick-walled pyrex tube is degassed wish nitrogen for 15 minutes. Pd(OAc)₂ (0.46 g, 2.05 mmol) and tri-o-tolylphosphine (1.25 g, 4.10 mmol) are placed into the tube, which is then sealed, and the mixture is heated to 100° for 5 hours. The mixture is diluted with EtOAc (400 mL), and white precipitate is filtered out. The filtrate is then washed with 1 N HCl (2×400 mL), H20 (1×100 mL) and brine (1×100 ni), dried over MgSO₄, and concentrated in vacuo. Chromatography (silica, 3:1 EtOAc/hexane) gives (E)-3-[4-(2,6-difluorobenzyloxy)-3-(2-hydroxyethyl)-phenyl]-2-butenoic acid diethy amide.

A solution of oxalyl chloride (1.04 mL, 11.9 mmol) in methylene chloride (50 mL) is cooled to −78°, and DMSO (1.69 mL, 23.82 mmol) is added dropwise, via syringe to the solution. After stirring an additional 5 minutes, (until no gas evolution is observed), a solution of (E)-3-[4-(2,6-difluorobenzyloxy-3-(2-hydroxyethyl)-phenyl]-2-butenoic acid diethyl amide (4.0 g, 9.93 mmol) in methylene chloride (100 mL) is added. The reaction is then stirred at −78° for 30 minutes, followed by addition of triethylamine (6.23 mL, 44.67 mmol) in one portion. The mixture is then warmed to room temperature, stirred for an additional 30 minutes, and quenched with H₂O (100 mL). The mixture is separated, and the organic phase is washed with water (1×100 mL) and brine (1×100 mL), dried over MgSO₄, and concentrated in vacuo to yield (E)-[5-(2-diethylcarbamoyl-1-methylvinyl)-2-(2,6-difluorobenzyloxy)-phenyl]-acetaldehyde.

(b) Similarly prepared is: (E)-[5(2-diethylcarbamoyl-1-methylvinyl)-2-(1-phenyl-ethoxy)-phenyl]-acetic acid; MS: 396 (M⁺+1), 292 (M⁺-PhCHCH₃⁺); ¹H NMR (CDCl₃): m (7H) @ 7.15–7.36 (arom H), d(1H) @ 6.61 (arom H).

EXAMPLE 9

(a) Similarly to procedure described in example 8, (E)-3-[4-(2,6-difluorobenzyloxy)-3-(3-oxopropyloxy)-phenyl]-2-butenoic acid diethyl amide is converted to (E)-3-[5-(2-di-ethylcarbamoyl-1-methylvinyl)-2-(2,6-difluorobenzyloxy)-phenoxy]-propionic acid; m.p.=138°–139°.

The starting material is prepared as follows:

A solution of 3'-hydroxy-4'-(2,6-(difluorobenzyloxy)-acetophenone (3.35 g, 12.05 mmol), 2-(3-bromopropoxy)-tetrahydropyran (2.69 g, 28.94 mmol) and in acetone (240 mL) is refluxed for 18 hours. At this time an additional amount of 2-(3-bromopropoxy)-tetrahydropyran (2.69 g, 28.94 mmol) and K₂CO₃ (1.66 g, 18.08 mmol) is added to the mixture, which is refluxed for an additional 6 hour. The mixture is filtered, and the filtrate is concentrated in vacuo. The residue is chromatographed (3:1 hexane/EtOAc) to yield 4'-(2,6-difluorobenzyloxy)-3'-[3-(tetrahydropyran-2-yloxy)-propoxy]-acetophenone.

To a solution of washed NaH (0.74 g, 30.94 mmol)) in THF (30 mL) is added a solution of diethyl [2-(diethylamino)-2-oxoethyl]-phosphonate (7.77 g, 30.94 mmol) in THF (30 mol), dropwise, and the solution is stirred at room temperature for 5 minutes until gas evolution ceases. A solution of 4'-(2,6-difluorobenzyloxy)-3'-[3-(tetrahydropyran-2-yloxy)-propoxy]-acetophenone (6.50 g, 15.47 mmol) in THF (30 mL) is then added over 5 minutes and the resulting mixture is refluxed for 18 hours. After cooling, the mixture is quenched with 30 mL saturated aqueous NH₄Cl, and is concentrated to 30 mL in vacuo. The residue is dissolved in EtOAc (50 mL), washed with H₂O (1×50 mL) and brine (1×50 ml), dried over MgSO$_4$, and concentrated in vacuo. Chromatography (silica, 3:1 hexane/ EtOAc) provides N,N-diethyl (E)-3-{4-(2,6-difluorobenzyloxy)-3-[3-(tetrahydropyran-2-yloxy)-propoxy]-phenyl}-2-butenamide.

To a solution of N,N-diethyl (E)-3-{4-(2,6-difluorobenzyloxy)-3-[3-(tetrahydropyran-2-yloxy)-propoxy]-phenyl}-2-butenamide (3.53 g, 6.83 mmol) in methanol (72 mL) is added 1N HCl (39.0 mL), and the resulting mixture is stirred for 1 hour. After this time, the solution is concentrated to 40 mL in vacuo, and the residue is extracted with EtOAc (2×75 mL). The combined organic phase is washed with water (1×100 mL) and brine (1×100 mL), dried over MgSO$_4$, and concentrated in vacuo to yield N,N-diethyl (E)-3-[4-(2,6-difluorobenzyloxy)-3-(3-hydroxypropoxy)-phenyl]-2-butenamide.

To a solution of diethyl (E)-3-[4-(2,6-difluorobenzyloxy)-3-(3-hydroxypropoxy)-phenyl]-2-butenamide (2.22 g, 5.13 mmol) and anhydrous sodium acetate (5.05 g, 61.53 mmol) in CH$_2$Cl$_2$ (100 mL) is added pyridinium dichromate (6.63 g, 30.76 mmol) and the mixture is stirred for 2.5 hours. At this time, 2 g celite is added to the mixture, and the resulting mixture is filtered through celite, and the solid is washed with CH$_2$Cl$_2$ (50 mL). The filtrate is concentrated in vacuo, and the residue is filtered through a column of florisil, yielding N,N-diethyl (E)-3-[4-(2,6-difluorobenzyloxy)-3-(3-oxopropyloxy)-phenyl]-2-butenamide, as a brown oil. This crude product is carried on directly to the next step.

(b) Prepared similarly is: (E)-3-[5-(2-diethylcarbamoyl-1-methylvinyl)-2-(1-phenylethoxy)-phenoxy]-propionic acid; MS: 426 (M$^+$+1), 322 (M$^+$-Ph(CH$_3$)CH). $^1$H NMR: t (2H) @ 4.32, 3.85.

EXAMPLE 10

(a) Similarly to procedure described in example 2, (E)-[5-(2-diethylcarbamoyl-1-methylvinyl)-2-(1-phenylethylthio)phenoxy]acetic acid ethyl ester is converted to (E)-[5-(2-diethylcarbamoyl-1-methylvinyl)-2-(1-phenylethylthio) phenoxy]acetic acid; m.p.=157°–159°.

The starting material is prepared as follows:

To a solution of acetovanillone (8.31 g, 50 mmol) and 2.81 g KOH (50 mmol) in H$_2$O (34 mL), at 0°, is added a solution of dimethylthiocarbamoyl chloride (8.28 g, 67 mmol) in THF (14 mL), dropwise, at such a rate as to keep the reaction temperature below 12°. The reaction mixture is warmed to room temperature, and stirred for 30 minutes. It is then diluted with 1 N NaOH (100 mL) and extracted with EtOAc (3×80 mL). The combined organic phase is washed with H$_2$O (1×100 mL) and brine (1×50 mL), dried over MgSO$_4$, and concentrated in vacuo to give dimethylthiocarbamic acid O-(4-acetyl-2-methoxy-phenyl) ester. To a thick walled pyrex tube is aded dimethylthiocarbamic acid O-(4-acetyl-2-methoxy-phenyl) ester (9.81 g, 38.77 mmol). The tube is flushed with nitrogen, sealed, and then heated to 250° for 1 hour. After cooling, the residue is chromatographed (silica gel, 1:1 EtOAc/hexane) to yield dimethylthiocarbamic acid S-(4-acetyl-2-methoxy-phenyl) ester.

To dimethylthiocarbamic acid S-(4-acetyl-2-methoxy-phenyl) ester (3.0 g, 11.86 mmol) in ethylene glycol (50 mL) is added KOH (1.0 g, 17.8 mmol) in H$_2$O (5 mL), and this mixture is refluxed for 1 hour. After cooling, this mixture is poured into 250 mL ice, and then washed with ether (3×75 mL). The aqueous phase is then acidified to pH 1 with conc. HCl, and the solution is filtered to remove precipitate. The aqueous layer is then extracted with EtOAc (3×75 mL), and the combined organic phase is washed with water (1×50 mL) and brine (1×50 mL), dried over MgSO$_4$, and removed in vacuo to yield 4-mercapto-3-methoxyacetophenone.

To 4-mercapto-3-methoxyacetophenone (0.865 g, 4.75 mmol) and (1-bromoethyl)-benzene (0.74 mL, 5.23 mmol) in acetone (40 mL) is added K$_2$CO$_3$ (0.985 g, 7.13 mmol), and the mixture is refluxed for 1.5 hours. After cooling, the mixture is filtered, and the acetone is removed in vacuo. The residue is then dissolved in EtOAc (50 'mL) and washed with H$_2$O (1×50 mL) and brine (1×50 mL), dried over MgSO$_4$, and the solvent is removed in vacuo. Chromatography (silica, 4:1 hexane/EtOAc) provides 4-(1-phenylethylthio)-3-methoxy-acetophenone. To a soution of washed NaH (0.283 g, 7.06 mmol) in THF (10 mL) is added a solution of diethyl [2-(diethylamino)-2-oxoethyl]-phosphonate (1.77 g, 7.06 mmol) in THF (10 mol), dropwise, and the solution is stirred at room temperature for 5 minutes, until gas evolution ceases. A solution of 4-(1-phenylethylthio)-3-methoxy-acetophenone (1.01 g, 3.53 mmol) in THF (20 mL) is then added over 5 minutes, and the resulting mixture is refluxed for 18 hours. After cooling, the mixture is quenched with 30 mL saturated aq. NH$_4$Cl, and is concentrated to 30 mL in vacuo. The residue is dissolved in EtOAc (50 mL), washed with H$_2$O (1×50 mL) and brine (1×50 mL), dried over MgSO$_4$, and concentrated in vacuo. Chromatography (silica, 2:1 hexane/EtOAc) provides (E)-3-[(4-mercapto-3-methoxy)-phenyl]-2-butenoic acid diethyl amide. To a solution of (E)-3-[(4-mercapto-3-methoxy)-phenyl]-2-butenoic acid diethyl amide (0.76 g, 1.98 mmol) in CH$_2$Cl$_2$ (25 mL), cooled to –78°, is added BBr$_3$ (0.75 mL, 7.94 mmol), slowly, via syringe. After stirring at –78° for 3 hours, the solution is poured onto ice (50 mL), acidified to pH 1 with 1 N HCl, and extracted with CH$_2$Cl$_2$ (2×25 mL). The combined organic phase is washed with water (1×50 mL) and brine (1×50 mL), dried over MgSO$_4$, and concentrated in vacuo, yielding (E)-3-[(4-mercapto-3-hydroxy)-phenyl]-2-butenoic acid diethyl amnide.

To a solution of (E)-3-[(4-(mercapto-3-hydroxy)-phenyl]-2-butenoic acid diethyl amide (0.81 g, 1.98 mmol) and (1-bromoethyl)benzene (0.28 mL, 1.98 mmol) in acetone (30 mL) is added K$_2$CO$_3$ (0.27 g, 1.98 mmol), and the mixture is refluxed for 1 hour. After cooling, the mixture is filtered, and the acetone is removed in vacuo. The residue is then dissolved in EtOAc (50 mL) and washed with H$_2$O (1×50 mL) and brine (1×50 mL), dried over MgSO$_4$, and the solvent is removed in vacuo. Chromatography (silica, 1:1 hexane/EtOAc) provides (E)-3-[4-(1-phenylethylthio)-3-hydroxyphenyl]-2-butenoic acid diethyl amide.

To a solution of (E)-3-[4-(1-phenylethylthio)-3-(1-hydroxyphenyl]-2-butenoic acid diethyl amide (0.40 g, 1.08 mmol) and ethyl bromoacetate (0.14 mL, 1.30 mmol)) in acetone (20 mL) is added K$_2$CO$_3$ (0.225 g, 1.63 mmol), and the mixture is refluxed for 2 hours. After cooling, the mixture is filtered, and the acetone is removed in vacuo. The residue is then dissolved in EtOAc (50 mL) and washed with H$_2$O (1×50 mL) and brine (1×50 ml), dried over MgSO$_4$, and the solvent is removed in vacuo, yielding (E)-[5-(2-diethylcarbamoyl-1-methylvinyl)-2-(1-phenylethylthio) phenoxy]-acetic acid ethyl ester.

Similarly prepared are:

(b) (E)-[5-(2-diethylcarbamoy-1-methylvinyl)-2-(diphenylmethylthio)phenoxy]-acetic acid; m.p. 175°–176°.

(c) (E)-[5-(2-diethylcarbamoyl-1-methylvinyl)-2-(benzylthio)phenoxy]-acetic acid; m.p. 132°–134°.

EXAMPLE 11

Similarly to the procedure described in example 8, N,N-diethyl (E)-3-[3-(3-hydroxypropyl)4-(1-phenylethoxy)- phenyl]-but-2-enamide is converted into (E)-3-[5-(2-diethylcarbamoyl-1-methylvinyl)-2-(1-phegylethoxy) phenyl]-propionic acid; MS: 412 (M$^+$+1), 308 (M$^+$-PhCHCH$_3{}^+$).

The starting material is prepared as follows:

A solution of 4hydroxyacetophenone (9.53 g, 70 mmol), allyl bromide (6.66 mL, 77 mmol), and K$_2$CO$_3$ (14.51 g, 105 mmol in acetone (150 mL) is refluxed 6 hours. The mixture is then filtered and the filtrate is concentrated in vacuo. The residue is dissolved in EtOAc (100 mL) and then washed with H$_2$O (1×100 mL) and brine (1×100 mL), and dried over MgSO$_4$. Concentration in vacuo yields 4'-allyloxyacetophenone.

A solution of 4'-allyloxyacetophenone (6.0 g, 34.1 mmol) in 10 mL xylene is introduced into a thick walled pyrex tube, which is sealed with a teflon cap. After heating to 230° for 5 hours, the solution is cooled to 0°. The precipitated white solid is filtered and the solid is washed with cold toluene and hexane to yield 3'-allyl-4'-hydroxyacetophenone.

A solution of 3'-allyl-4'-hydroxyacetophenone (3.46 g, 19.66), (1-bromoethyl)-benzene (3.05 mL, 21.63 mmol)), and K$_2$CO$_3$ (4.07 g, 29.49 mmol) in acetone (100 mL) is refluxed 20 hours. The mixture is then filtered and the filtrate is concentrated in vacuo. The residue is dissolved in EtOAc (100 mL) and then washed with H$_2$O (1×100 mL) and brine (1×100 mL), dried over MgSO$_4$, and concentrated in vacuo. Chromatography (5:1 hexane/EtOAc) yields 3'-allyl-4'-(1-phenylethoxy)-acetopbenone. To a solution of sodium hydride (0.54 g, 13.5 mmol) in THF (20 mL) is added a solution of ethyl [2-(diethylamino)-2-oxoethyl]-phosphonate (3.13 g. 12.5 mmol) in THF (20 ml). After stirring this mixture for 5 minutes. at room temperature, a solution of 3'-allyl-4'-(1-phenylethoxy)-acetophenone (2.91 g, 10.4 mmol) in ThF (30 mL) is added, and the solution is refluxed 18 hours. After cooling, the mixture is then quenched with saturated aqueous ammonium chloride (50 mL), and extracted with ethyl acetate (4×75 mL). The combined organic phase is washed with water (1×100 mL) and brine (1×100 mL), dried over MgSO$_4$, concentrated in vacuo, chromatographed (silica, 2:1 EtOAc/hexane) to yield N,N-diethyl (E)-3-[3-allyl 4-(1-phenylethoxy)-phenyl)-but-2-enamide.

To a solution of N,N-diethyl (E)-3-[3-allyl-4-(1-phenylethoxy)-phenyl]-but-2-enamide (2.61 g, 6.92 mmol) and Wilkinson's catalyst (tris(triphenylphosphine)rhodium (I) chloride, 64 mg, 0.069 mmol) in THF(40 mL) at 0° is added a 1.0 M solution of catecholborane in THF (7.62 mL, 7.62 mmol), via syringe. After stirring for 3 hours at 0°, the solution is quenched with methanol (15 mL), followed by addition of a solution 30% hydrogen peroxide (1.94 mL) in 3 M NaOH (18 mL). The solution is then warmed to room temperature over 3 hours. The solution is concentrated to 25 mL in vacuo, and the residue is taken up in H$_2$O (100 ML) and extracted with ether (3×50 mL). The combined organic phase is washed with water (1×50 mL) and brine (1×50 mL), dried over MgSO$_4$, and concentrated in vacuo. Chromatography (silica, 4:1 EtOAc/hexane) yields N,N-diethyl (E)-3-[3-(3-hydroxypropyl)4-(1-phenylethoxy)-phenyl]-but-2-enamide.

EXAMPLE 12

To a solution of NaH (0.10 g, 2.4 mmol) in THF (15 mL) is added a solution of diethyl [2-(diethylamino)-2-oxoethyl]-piosphonate (0.30 g, 1.2 mmol) dropwise, and the solution is stirred at room temperature for 5 minutes, until gas evolution ceases. A solution of t-butyl [5-acetyl-2-phenethylphenoxy]-acetate (1.01 g, 3.53 mmol) in THF (5 mL) is then added over 5 minutes, and the resulting mixture is refluxed for 4 hours. After cooling, the mixture is quenched with 30 mL saturated 1 N HCl, and extracted with ether (2×30 mL), washed with brine (1×50 mL), dried over MgSO$_4$, and concentrated in vacuo. Chromatography (silica, 20:1 CH$_2$Cl$_2$/methanol, 0.5% acetic acid) provides (E)-[5-(2-diethylcarbamoyl-1-methylvinyl)-2-phenethylphenoxy]-acetic acid; MS: 396 (M$^+$+1).

The starting material is prepared as follows:

A solution of 3'-hydroxy4'-benzyloxyacetophenone (3.5 g, 14.4 mmol), t-butyl bromoacetate (2.8 mL, 17.0 mmol), and K$_2$CO$_3$ (2.3 g, 17.0 mmol) in 100 mL acetone is refluxed 18 hours. After cooling, the mixture is filtered, and the acetone is removed in vacuo. The residue is then dissolved in EtOAc (50 mL) and washed with H$_2$O (1×50 mL) and brine (1×50 mL), dried over MgSO$_4$, and the solvent is removed in vacuo. Chromatography (silica, 5:1 hexane/EtOAc) yields t-butyl (4-acetyl-2-benzyloxyphenoxy)-acetate.

To a solution of t-butyl (5-acetyl-2-benzyloxyphenoxy)-acetate (2.0 g, 5.6 mmol) in EtOH (25 mL) is added 10% Pd/C (0.10 g), and the mixture is hydrogenated at 1 atm for 1.25 hours. Filtration through celite, followed by solvent removal in vacuo yields t-butyl (5-acetyl-2-hydroxyphenoxy)-acetate.

A solution of t-butyl (5-acetyl-2-hydroxyphenoxy)-acetate (1.5 g, 5.6 mmol) and pyridine (1.2 mL, 15.0 mmol) in CH$_2$Cl$_2$ (20 mL) is cooled to −30°, and triflic anhydride (1.5 g, 5.6 mmol) is added via syringe ovr 2 minutes. After stirring 10 minutes H$_2$O (20 mL) is added, the solution is warmed to room temperature, and the solution is washed with 1 N HCl (1×50 mL) and brine (1×50 ml), dried over MgSO$_4$, and concentrated in vacuo. Chromatography (silica, 5:1 hexane/EtOAc) yields t-butyl {5-acetyl-2-[(trifluoromethyl)sulfonyloxy]-phenoxy}acetate.

A solution of t-butyl { 5-acetyl-2[(trifluoromethyl) sulfonyloxy]-phenoxy}acetate(1.0 g, 1.3 mmol) and phenylacetylene (0.33 mL, 3.0 mmol) in 20 mL triethylamine in a thick walled pyrex tube is degassed with nitrogen for 15 minutes. Bis(triphenylphosphine)-palladium(II) chloride (35 mg, 0.05 mmol) and copper (I) iodide (10 mg, 0.05 mmol) are added, and the vessel is sealed, and heated to 60° for 18 hours. After cooling, the triethylamine is removed in vacuo, and the residue is dissolved in ether (100 mL) and washed with 1 N HCl (1×100 mL) and brine (1×50 mL), dried over MgSO$_4$, and concentrated in vacuo. Chromatography (silica, 5:1 hexane/EtOAc) yields t-butyl [5-acetyl-2-(2-phenylethynyl)-phenoxy]-acetate, along with 10% starting material. This mixture is carried on to the next step.

t-Butyl (E)-[5-acetyl-2-(2-phenylethynyl)-phenoxy]-acetate (0.2 g, 0.56 mmol) is dissolved in 5 mL THF, and then diluted with EtOH (15 mL). 10% Pd/C (0.10 g) is added, and the mixture is hydrogenated at 1 atm until theoretical amount of hydrogen is consumed. Filtration through celite, followed by solvent removal in vacuo yields t-butyl [5-acetyl-2-phenethylphenoxy]-acetate.

EXAMPLE 13

Similarly to procedure described in example 2, (E)-5-(2-diethylcarbamoyl-1-methylvinyl)-2-(1-phenylethoxy) benzoic acid ethyl ester is converted to (E)-5-(2-diethylcarbamoyl-1-methylvinyl)-2-(1-phenylethoxy)benzoic acid, MS: 382 (M$^+$+1), 278 (M$^+$-PhCHCH$_3{}^+$).

The starting material is prepared as follows:

A solution of methyl 5-bromosalicylate (12.70 g, 55 mmol), (1-bromoethyl)benzene (7.05 mL, 50 mmol), and $K_2CO_3$ (20.73 g, 150 mmol) in acetone (250 mL) is refluxed 18 hours. The mixture is then filtered and the filtrate is concentrated in vacuo. The residue is dissolved in EtOAc (250 mL) and then washed with 1 N NaOH (2×150 mL) and brine (1×100 mL), and dried over $MgSO_4$. Concentration in vacuo yields methyl 5-bromo-2-(1-phenylethoxy)-benzoate.

A solution of methyl 5-bromo-2-(1-phenylethoxy)-benzoate (3.35 g, 10.0 mmol) and crotonic acid (1.72 g, 20.0 mmol) in 8 mL triethylamine in a thick-walled pyrex tube is degassed with nitrogen for 15 minutes. $Pd(OAc)_2$ (0.112 g, 0.50 mmol) and tri-o-tolylphosphine (0.304 g, 1.0 mmol) are placed into the tube, which is then sealed, and the mixture is heated to 100° for 5 hours. The mixture is diluted with EtOAc (300 mL), and white precipitate is filtered. The filtrate then washed with 1 N HCl (2×150 mL), and brine (1×50 mL), dried over $MgSO_4$, and concentrated in vacuo to give methyl (E)-5-(2-carboxy-1-methylvinyl)-2-(1-phenylethoxy)-benfoate.

To a solution of methyl E)-5-(2 arboxy-1-methylvinyl)-2-(1-phenylethoxy)benzoate (1.0 g, 2.94 mmol) in 40 mL $CH_2Cl_2$ at 0° is added oxalyl chloride (1.03 mL, 11.76 mmol followed by dimethyl formamide (50 μL). The solution is then warmed to room temperature over 1 hour. Concentration in vacuo yields methyl (E)-5-(2-chlorocarbonyl-1-methylvinyl)-2-(1-phenylethoxy)-benzoate.

To a solution of methyl (E)-5-(2-chlorocarbonyl-1-methylvinyl)-2-(1-phenylethoxy)-benzoate (1.0 g, 2.79 mmol)in THF (50 mL) is added diethylamine (1.16 mL, 11.8 mmol), and the mixture is stirred at room temperature for 3 hours, after which time THF is removed in vacuo, and the residue is lssoved in $CH_2Cl_2$ (75 mL) and then washed with 1 N HCl (2×100 mL) and brine (1×50 mL), and dried over $MgSO_4$. Chromatography (silica, 2:1 hexane/EtOAc) yields methyl (E)-5-(2-diethylcarbamoyl-1-methylvinyl)-2-(1-phenylethoxy)-benzoate.

EXAMPLE 14

Similarly to the procedures desinbed in examples 1 and 2, 1-[6-(2,6-difluorobenzyl-oxy)-5-hydroxypyridin-3-yl]-ethanone is converted to (E)-[5-(2-diethylcarbamoyl-1-methylvinyl)-2-(2,6-difluorobenzyloxy)-pyridin-3-yloxy]-acetic acid, m.p.=156°–157°.

The starting material is prepared as follows:

To a solution of 5-bromo-3-hydroxy-2(1H)-pyridinone (U.S. Pat. No. 3,471,506, 10.0 g, 52.6 mmol) in dioxane (30 mL) and $H_2O$ (15 mL) was added NaOH (2.1 g, 52.5 mol) dissolved in $H_2O$ (12.5 mL). To this mixture is added di-t-butyl-dicarbonate (12.5 g, 57.5 mmol), and the mixture is stirred at room temperature for 6 hours. At this time, the mixture is filtered, and the solid is washed with $H_2O$ (50 mL), and is dissolved in $CH_2Cl_2$ (100 mL). This organic solution is washed with brine, dried over $MgSO_4$, and concentrated to yield 5-bromo-3-(t-butoxycarbonyloxy)-2 (1H)pyridinone. A solution of 5-bromo-3-(t-butoxycarbonyloxy)-2(1H)-pyridinone (5.0 g, 17.2 mmol), $AG_2CO_3$ (4.74 g, 17.2 mmol) and α-bromo-2,6-difluorotoluene (3.56 g, 17.2 mmol) in toluene (60 mL) is heated to 42° for 24 hours in the dark. At this time the mixtut is filtered. The filtrate is concentrated in vacuo, and the residue is dissolved in EtOAc (150 mL) and washed with $H_2O$ (50 mL) and brine (50 mL), dried over $MgSO_4$ and concentrates in vacuo. Chromatography (silica, 9:1 EtOAc/hexane) yields 5-bromo-3-(t-butoxycarbonyloxy)-2-(2,6-difluorobenzyloxy)-pyridine.

A solution of 5-bromo-3-(t-butonycarbonyloxy)-2-(2,6-difluorobenzyloxy)-pyridine (3.60 g, 8.65 inmol) and CuCN (2.31 g, ;5.9 mmol) in dimethylformamide (86 mL) is refluxed for 10 hours. The mixture is the poured into a solution of saturated $NH_3$ (10 ml) in ice (100 mL), and the resulting mixture is extracted with EtOAc (2×75 mL). The combined organic phase is washed with water (1×50 mL) and brine (1×50 ml), dried over $MgSO_4$, and concentrated in vacuo. Chromatography (silica, 3:1 EtOAc/hexane) yields 6-(2,6-di-fluorobenzyloxy)-5-hydroxynicotinontpile.

To a solution of 6(2,6-difluorobenzyloxy)-5-hydroxynicotinonitrile (0.60 g, 2.29 mmol) in THF (20 ml) is added a 3.0 M solution of MeMgBr in ether (5.28 ml, 15.8 mmol) at 0°, and the solution is warmed to room temperature for 5 hours, after which time the mixture is quenched with 10% aq. HCl, (10 mL), and extracted with ether (3×30 ml). The combined organic phase is washed with water (1×50 mL) and brine (1×50 mL), dried over $MgSO_4$, and concentrated in vacuo to yield 1-[6-(2,6-difluorobenzyloxy)-5-hydroxypyridin-3-yl]-ethanone.

EXAMPLE 15

(a) Similarly to the procedure described in example 2, ethyl (Z)-[5-(2-diethylcarbamoyl-1-methylvinyl)2-(1-phenylethoxy)-phenoxy]-acetate (the minor isomer isolated from chromatography in the final step of example 1), is converted into (Z)-[5-(2-diethylcarbamoyl-1-methylvinyl)-2-(1-phenylethoxy)-phenoxy]-acetic acid; MS: 412 ($M^+$+1), 308 ($M^+$-Ph($CH_3$)CH). $^1$H NMR:s (1H) @ 5.82.

Prepared similarly are:

(b) (Z)-[5-(2-diethylcarbamoyl-1-methylvinyl)-2-(2-bromobenzyloxy)-phenoxy]-acetic acid; m.p.=108°–110 °.

(c) (Z)-[5-(2-diethylcarbamoyl-1-methylvinyl)-2-(2-methylbenzyloxy)-phenoxy]-acetic acid; m.p.=132°–135°.

EXAMPLE 16

(a) Similarly to the procedure described in example 2, methyl (E)-(R)-(-)-[5-(2-diethylcarbamoyl-1-methylvinyl)-2-(1-phenylethoxy)-phenyl]-acetate is converted into (E)-(R)-(-)-[5-(2-diethylcarbamoyl-1-methylvinyl1)-2-(1-phenylethoxy)-phenyl]-acetic acid, MS: 396 ($M^+$+1), 292 ($M^+$-Ph($CH_3$)CH. $[\alpha]_D$=−10.341 (c=0.80, MeOH), 97% ee by NMR.

The starting material is prepared a follows:

To a solution of 2-hydroxyphenylacetic acid (5.0 g, 32.8 mmol) in MeOH (100 mL) at 0° C. is added tetra-N-butyl-ammonium tribomide (15.8 g, 32.8) in one portion (residual compound is rinsed in with 20 mL MeOH. The solution is then warmed to room temperature and stirred overnight, during which time the solid slowly dissolves. MeOH is then evaporated, and the residue is taken up in 10% aqueous $NaHSO_3$ (100 mL) and 5:1 $Et_2O$/EtOAC (300 mL). The organic layer is separated and washed with saturated aqueous $NaHCO_3$ (100 mL), brine (50 mL) and dried ($MgSO_4$). Evaporation yields a semisolid, which is recrystallized from $Et_2O$/hexane to yield methyl 4-bromo-2-hydroxyphenylacetate, as an off-white solid.

To a solution of methyl 4-bromo-2-bydroxyphenylacetate (1.0 g, 4.1 mmol), (S)-(-)-phenethyl alcohol (0.50 g, 4.1 mmol) and triphenylphosphine (1.07 g, 4.1 mmol) in toluene (1 5 mL) at 0° C. is added a solution of diethyl azodicarboxylate (4.1 mmol, 0.64 mL) in toluene (5 mL), dropwise, over 5 minutes. The solution is then warmed slowly to room temperature overnight. It is then diluted with toluene (30 mL), and 10 g Panther Creek clay is added. The mixture is stirred for 1 hour, then filtered, and the filtrate is evaporated and the residue chromatographed (silica, 10% ethyl acetate/hexane) to yield methyl (R)4-bromo-2-(1-phenylethoxy)-phenylacetate, as a clear thick oil.

A solution of methyl (R)4-brom-2-(1-phenylethoxy)-phenylacetate (0.50 g, 1.43 mmol) and diethylcrotonamide (0.30 g, 2.1 mmol) in triethylamine (5 mL) is deoxygenated with bubbling $N_2$ for 10 minutes in a small pressure tube. Palladium (II) acetate (16 mg, 0.07 mmol) and tris-(o-tolyl)-phosphine (44 mg, 0.14 mmol) is then added. The tube is then sealed, and the mixture heated to 100° C. for 2.5 hours. After cooling, the mixture (now dark, with precipitate present) is diluted with ethyl acetate (20 mL), and the mixture is filtered through celite, and the filtrate evaporated and chromatographed (silica, 30% ethyl acetate/hexane) to yield methyl (E)-(R)-(−)-[5-(2-diethylcarbamoyl-1-methylvinyl)-2-(1-phenylethoxy)-phenyl]-acetate as a yellow oil.

Prepared similarly is:

(b) (E)-(S)-(+)-[5-(2-diethylcarb 1-methylvinyl)-2-(1-phenylethoxy)-phenyl]-acetic acid, sodium salt, mp=115°–117°, $[\alpha]_D$=+19.59 (c=1.09, MeOH), 92% ee by NMR.

EXAMPLE 17

To a solution of (E)-[5-(2-diethylcarbamoyl-1-methylvinyl)-2-(1-phenylethylthio)-phenoxy]acetic acid ethyl ester (see example 10, 0.19 g, 0.42 mmol) in methanol (12 ml) at 0° C. is added a solution of potassium peroxymonosulfate (Oxone®) (0.77 g, 1.25 mmol) in water (12 ml), dropwise, over 5 minutes. The resulting mixture is then stirred at room temperature overnight. The mixture is diluted with water (50 ml) and then extracted with ethyl acetate (2×25 ml). The combined organic layers are washed with water (1×30 ml) and brine (1×30 ml), dried $MgSO_4$) and evaporated to yield (E)-[5-(2-diethylcarbamoyl-1-methylvinyl)-2-(1-phenylethylsulfonyl)phenoxy]acetic acid ethyl ester, as a clear oil.

EXAMPLE 18

Similarly to the procedure described in example 2, (E)-[5-(2-diethylcarbamoyl-1-methylvinyl)-2-(1-phenylethylsulfonyl)phenoxy]acetic acid ethyl ester (Example 17) is converted to (E)-[5-(2-diethylcarbamoyl-1-methylvinyl)-2-(1-phenylethylsulfonyl)phenoxy]-acetic acid, m.p.=198–200° C.

What is claimed is:

1. A compound of the formula

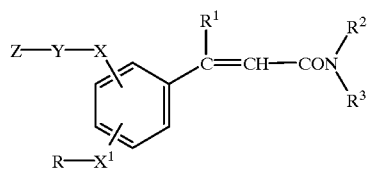

(II)

or of the formula

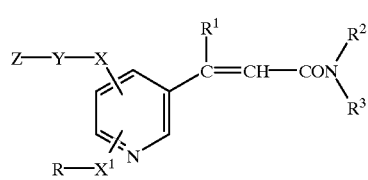

(III)

wherein in formula II the substituents —X—Y—Z and —$X^1$—R are located at the meta (3) and para (4) positions or at the two meta (3 and 3') positions and wherein in formula III the said substituents are at adjacent 5 and 6 positions of the pyridine ring;

R is (mono or di-carbocyclic or heterocyclic aryl)-lower alkyl;

$R^1$ is hydrogen or lower alkyl;

$R^2$ and $R^3$ are hydrogen, lower alkyl, lower alkoxy-lower alkyl or aryl-lower alkyl;

or $R^2$ and $R^3$ together with the nitrogen to which they are attached represent pyrrolidino, piperidino, or morpholino;

X is O, S or a direct bond;

$X^1$ is O, S or a direct bond;

Y is a direct bond, lower alkylene or lower alkylidene; and

Z is carboxyl, 5-tetrazolyl, hydroxymethyl or carboxyl derivatized in form of a pharmaceutically acceptable ester; or a pharmaceutically acceptable salt thereof.

2. A compound according to claim 1 of the formula

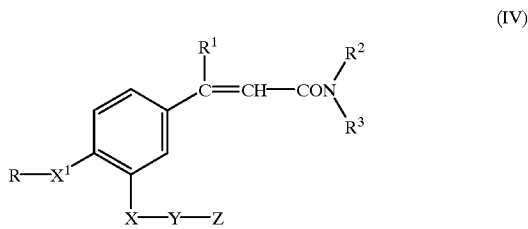

(IV)

or of the formula

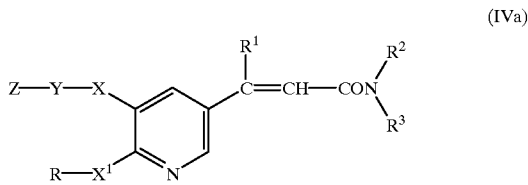

(IVa)

wherein R is (mono- or di-carbocyclic or heterocyclic aryl)-lower alkyl;

$R^1$ is hydrogen or lower alkyl;

$R^2$ and $R^3$ are hydrogen, lower alkyl, lower alkoxy-lower alkyl or aryl-lower alkyl;

or $R^2$ and $R^3$ together with the nitrogen to which they are attached represent pyrrolidino, piperidino or morpholino;

X is O, S or a direct bond;

$X^1$ is O, S or a direct bond;

Y is $C_1$–$C_4$-alkylene or $C_1$–$C_4$-alkylidene;

Z is carboxyl, 5-tetrazolyl, hydroxymethyl or carboxyl derivatized in form of a pharmaceutically acceptable ester;

or a pharmaceutically acceptable salt thereof.

3. A compound according to claim 2 which is the E-isomer of a compound of formula IVa or a pharmaceutically acceptable salt thereof.

4. A compound of the formula

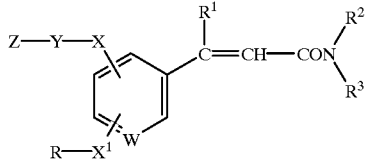

(Ia)

wherein W is CH or N;

R is (mono- or di-carbocyclic aryl or mono- or di-heterocyclic aryl)-lower alkyl;

$R^1$ is hydrogen or lower alkyl;

$R^2$ and $R^3$ hydrogen, lower alkyl, lower alkoxy-lower alkyl or aryl-lower alkyl;

or $R^2$ and $R^3$ joined together represent lower alkylene optionally interrupted by O, NH, N-lower alkyl or S so as to form a ring with the amide nitrogen;

X is O, S, SO, $SO_2$ or a direct bond;

$X^1$ is O, S, SO, $SO_2$ or a direct bond;

Y is a direct bond, lower alkylene or lower alkylidene; and

Z is carboxyl, 5-tetrazolyl, hydroxymethyl or carboxyl derivatized in form of a pharmaceutically acceptable ester;

or a pharmaceutically acceptable salt thereof.

5. A compound according to claim 2 which is the (E)-isomer of a compound of formula IV in which the substituted phenyl and the

groups are trans to each other, of the formula

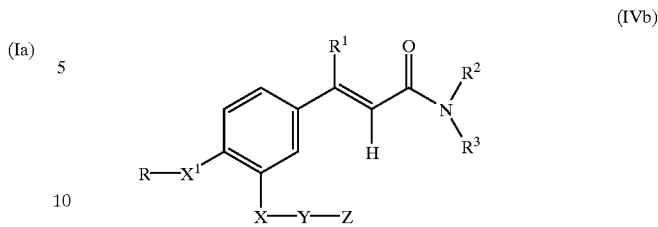

(IVb)

or a pharmaceutically acceptable salt thereof.

6. A compound according to claim 5 wherein R is (mono- or di-carbocyclic aryl)-lower alkyl; $R^1$ is lower alkyl; $R^2$ and $R^3$ represent lower alkyl; X represents O or a direct bond; $X^1$ represents O; Y represents $C_1$–$C_4$ alkylene or $C_1$–$C_4$-alkylidene; Z represents carboxyl or 5-tetrazolyl; or a pharmaceutically acceptable salt thereof.

7. A compound according to claim 6 which is (E)-[5-(2-diethylcarbamoyl-1-methylvinyl)-2-(2,6-difluorobenzyloxy)-phenoxy]-acetic acid or a pharmaceutically acceptable salt thereof.

8. A compound according to claim 6 which is (E)-[5-(2-diethylcarbamoyl-1-methylvinyl)-2(2,6-difluorobenzyloxy)-phenyl]-acetic acid or a pharmaceutically acceptable salt thereof.

9. A compound according to claim 6 which is (E)-[5-(2-diethylcarbamoyl-1-methylvinyl)-2-(1-phenylethoxy)-phenyl]acetic acid or a pharmaceutically acceptable salt thereof.

10. A pharmaceutical composition for antagonizing LTB-4 in mammals comprising an effective LTB-4 antagonizing amount of a compound of claim 4 and a pharmaceutically acceptable carrier.

11. A method of antagonizing LTB-4 activity in mammals which comprises administering to a mammal in need thereof an effective LTB-4 antagonizing amount of a compound according to claim 4.

12. A method of treating LTB-4 dependent conditions in mammals which comprises administering to a mammal in need thereof an effective LTB-4 antagonizing amount of a compound according to claim 4.

* * * * *

UNITED STATES PATENT AND TRADEMARK OFFICE
CERTIFICATE OF CORRECTION

PATENT NO. : 6,291,530 B1
DATED : September 18, 2001
INVENTOR(S) : Greenspan et al.

It is certified that error appears in the above-identified patent and that said Letters Patent is hereby corrected as shown below:

<u>Title page,</u>
Items [22], [86] and [87], should read

-- [22] PCT Filed: September 24, 1997

[86] PCT No.: PCT/EP 97/05255
    § 371 (c) (1),
    (2), (4) Date: March 23, 1999

[87] PCT Pub. No. WO 98/13347
    PCT Pub. Date: April 2, 1998 --.

Signed and Sealed this

Twenty-first Day of October, 2003

JAMES E. ROGAN
*Director of the United States Patent and Trademark Office*